United States Patent
Ding et al.

(10) Patent No.: US 11,530,196 B2
(45) Date of Patent: Dec. 20, 2022

(54) PYRIMIDINE COMPOUND ACTING ON EGFR AND ERBB2

(71) Applicant: CHINA RESOURCES PHARMACEUTICAL HOLDINGS COMPANY LIMITED, Beijing (CN)

(72) Inventors: Charles Z. Ding, Shanghai (CN); Lu Zhang, Shanghai (CN); Xile Liu, Shanghai (CN); Lihong Hu, Shanghai (CN); Wen Jiang, Shanghai (CN); Jian Li, Shanghai (CN); Shuhui Chen, Shanghai (CN)

(73) Assignee: CHINA RESOURCES PHARMACEUTICAL HOLDINGS COMPANY LIMITED, Beijing (CN)

( * ) Notice: Subject to any disclaimer, the term of this patent is extended or adjusted under 35 U.S.C. 154(b) by 0 days.

(21) Appl. No.: 17/629,844

(22) PCT Filed: Jul. 24, 2020

(86) PCT No.: PCT/CN2020/103985
§ 371 (c)(1),
(2) Date: Jan. 25, 2022

(87) PCT Pub. No.: WO2021/018017
PCT Pub. Date: Feb. 4, 2021

(65) Prior Publication Data
US 2022/0289714 A1    Sep. 15, 2022

(30) Foreign Application Priority Data
Jul. 26, 2019   (CN) .......................... 201910684658.1

(51) Int. Cl.
C07D 403/04   (2006.01)
A61P 35/00    (2006.01)

(52) U.S. Cl.
CPC ............ *C07D 403/04* (2013.01); *A61P 35/00* (2018.01)

(58) Field of Classification Search
CPC .............................. C07D 403/04; A61P 35/00
See application file for complete search history.

(56) References Cited

U.S. PATENT DOCUMENTS 10,227,342 B2    3/2019   Huang et al.

FOREIGN PATENT DOCUMENTS

| CN | 103565653 | * | 2/2014 | ............. A61Q 19/00 |
| CN | 103565653 A | | 2/2014 | |

OTHER PUBLICATIONS (Zhuang, Wu et al.), "Clinical Efficacy of Icotinib in Patients with Advanced Nonsmall Cell Lung Cancer Harboring EGFR Exon 20 Mutations", (Journal of Clinical and Pathological Research), vol. 37, No. 2,, Dec. 31, 2017 (Dec. 31, 2017), ISSN: 2095-6959, 282-288.
International Search Report and Written Opinion of PCT/CN2020/103985 dated Feb. 4, 2021.
International Search Report and Written Opinion of PCT/CN2020/103985 dated Oct. 29, 2020.
Extended European Search Report issued in corresponding European Application No. 2048095.4, dated Aug. 5, 2022.

* cited by examiner

*Primary Examiner* — Erich A Leeser
(74) *Attorney, Agent, or Firm* — Harness, Dickey & Pierce, P.L.C.

(57) ABSTRACT

Disclosed is a pyrimidine compound acting on an EGFR exon 20 insertion mutation and an ERBB2 exon 20 insertion mutation or a pharmaceutically acceptable salt thereof.

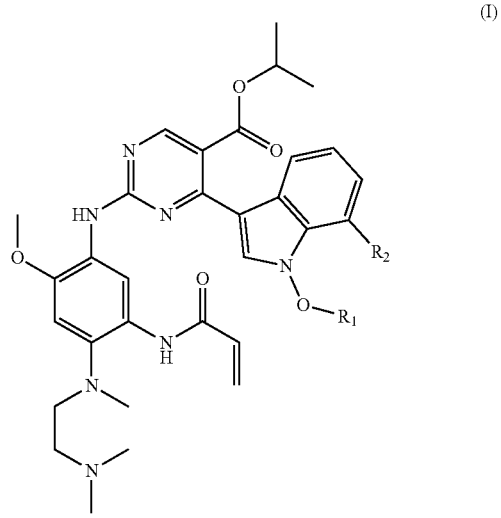

(I)

7 Claims, 3 Drawing Sheets

PYRIMIDINE COMPOUND ACTING ON EGFR AND ERBB2

CROSS-REFERENCE TO RELATED APPLICATIONS

This application is a U.S. National Phase Application under 35 U.S.C. 371 of International Application No. PCT/CN2020/103985, filed on Jul. 24, 2020, which claims the benefit of Chinese Patent Application No. 201910684658.1, filed on Jul. 26, 2019. The entire disclosures of the above applications are incorporated herein by reference.

TECHNICAL FIELD

The present disclosure relates to a class of pyrimidine compounds and pharmaceutically acceptable salts thereof that act on EGFR exon 20 insertion mutations and ERBB2 exon 20 insertion mutations.

PRIOR ART

Lung cancer is one of the most common malignancies, with 1.6 million new lung cancer cases worldwide each year, accounting for 13% of all malignancies, and there are 1.4 million deaths due to lung cancer each year. As the world's leading cancer killer, the incidence of lung cancer is still on the rise worldwide in recent years. Non-small cell lung cancer (NSCLC) accounts for approximately 85% of all lung cancers. Since patients with NSCLC do not have distinctive features in the early stages, most patients are already at an advanced stage at the time of diagnosis, and 65% of NSCLC are already lost the opportunity to surgery at the time of diagnosis. Therefore, drug therapy, namely chemotherapy and targeted therapy, is essential for the treatment of patients with advanced NSCLC.

EGFR is a major member of the ErbB family of tyrosine kinase receptors, the ErbB family includes ErbB1 (EGFR or HER1), ErbB2 (HER2), ErbB3 (HER3) and ErbB4 (HER4). EGFR consists of an extracellular ligand-binding domain, an α-helical transmembrane domain, an intracellular tyrosine kinase domain, and a carboxy-terminal region containing an autophosphorylation site. When the ligand binds to the receptor, it causes EGFR dimerization, activates intracellular protein tyrosine kinase activity, causes autophosphorylation of tyrosine residues, recruits related signaling proteins, and causes activation of downstream ERK/MAPK, PI3K/Akt and STAT signaling pathway, thereby regulating tumor cell proliferation, survival, differentiation, metastasis and tumor angiogenesis. Therefore, targeted therapy against EGFR can inhibit the transmission of downstream signaling pathways to inhibit tumor growth and differentiation.

EGFR Exon 20 insertion mutation is the third largest series of EGFR gene mutations in NSCLC, accounting for about 4%-7% of the entire EGFR mutations, and the amino acid sites translated in exon 20 are 762-823. The glutamate Glu762 starting at the N-terminus is an important catalytic site, followed by Ala763-Met766, the C-helix of the EGFR tyrosine kinase domain, which plays an important role in phosphate transfer. EGFR exon 20 insertion mutations mostly occur in Asian, female, non-smoking, and adenocarcinoma populations, and have the same clinical and pathological features as classical EGFR mutations. The most common type of mutation in exon 20 is Asp770_Asn771insSerValAsp, followed by Val769_Asp770insAlaSerVal, Asp770_Asn771insSerValAsp, Ala767_Val769dupAlaSerVal, Val769_Asp770insAlaSerVa and Ser768_Asp770dupSerValAsp, they have similar insertion sequence, accounting for 36% of the exon 20 mutations. In addition, the main mutation type is His773_Val774insAsnProHis, accounting for about 14% of exon 20 mutations.

HER2 Exon 20 insertion mutations account for more than 95% of all HER2 mutation types, wherein among HER2 exon 20 insertion mutation types, A775_G776_ins YVMA accounting for 85%, which is the most common mutation type.

There are currently no targeted drugs on the market that effectively inhibit EGFR and HER2 exon20 insertion mutations. In clinical studies, the marketed EGFR TKIs such as (Erlotinib/Gefitinib/Afatinib) lack efficacy and have low response rates against either EGFR or HER2 Exon20 insertion mutations. For example, the PFS of patients with EGFR Exon20 insertion mutation is only 2 months, which is much lower than that of patients with traditional mutations (Exon19 deletion & L858R). Second-generation EGFR inhibitors, such as afatinib and dacomitinib, have also been clinically reported to be less effective against exon 20 insertion mutations, so there is a large unmet clinical need for EGFR and HER2 exon 20 insertion mutations.

The EGFR and HER2 exon 20 insertion mutation inhibitor TAK788 developed by Japan's Takeda Pharmaceutical has shown good efficacy in preclinical and clinical phase I/II for non-small cell lung cancer with EGFR and HER2 exon 20 insertion mutation. According to clinical reports, the objective response rate of TAK788 is 43% and the disease control rate of TAK788 is 86%. The safety is similar to other marketed EGFR-TKIs, and TAK788 has a good prospect for the treatment of EGFR and HER2 exon 20 insertion mutations.

Content of the Present Invention

The present disclosure provides a compound represented by formula (I) or a pharmaceutically acceptable salt thereof,

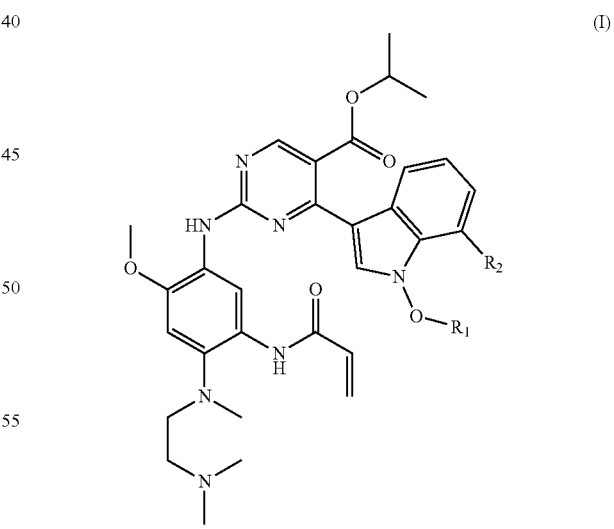

wherein, $R_1$ is selected from $C_{1-3}$ alkyl, $R_2$ is selected from H, F, Cl, Br, I, $C_{1-3}$ alkyl and cyclopropyl.

In some embodiments of the present disclosure, the $R_1$ is selected from methyl, ethyl and isopropyl, and other variables are as defined herein.

In some embodiments of the present disclosure, the $R_2$ is selected from H, Cl and cyclopropyl, and other variables are as defined herein.

There are still some solutions of the present disclosure which are obtained by any combination of the above variables.

The present disclosure also provides a compound represented by the following formula or a pharmaceutically acceptable salt thereof,

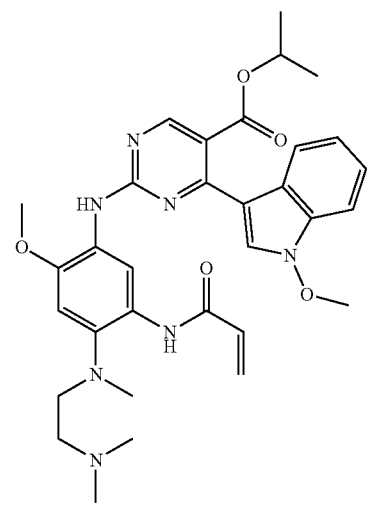

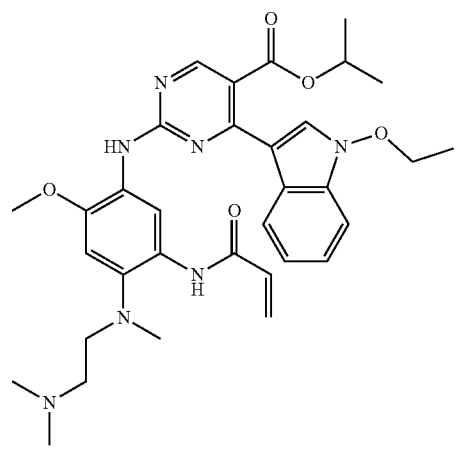

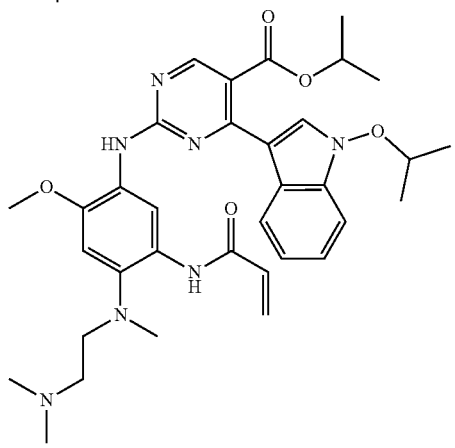

-continued

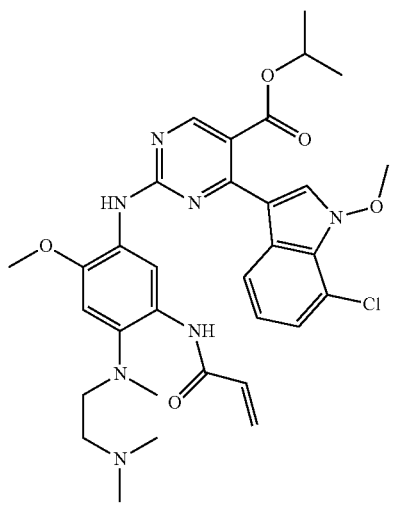

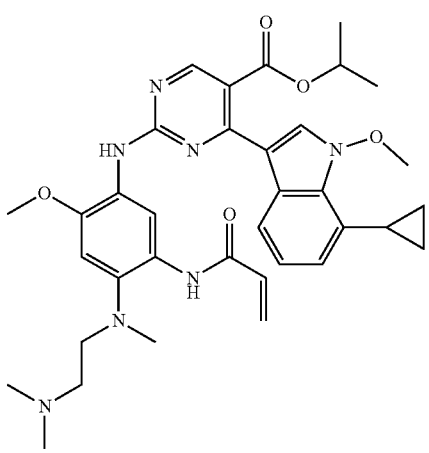

In some embodiments of the present disclosure, the pharmaceutically acceptable salt thereof is selected from

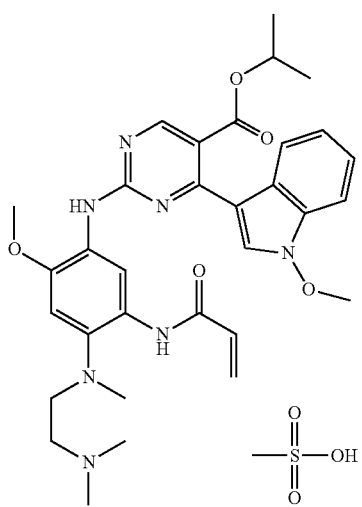

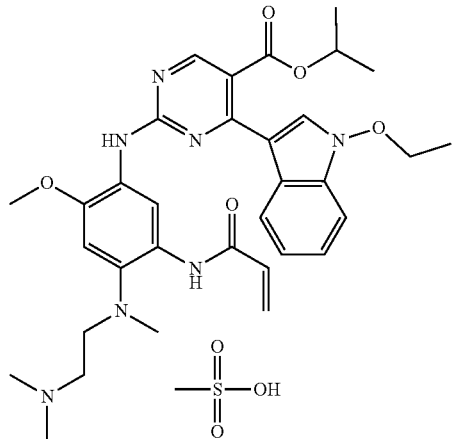

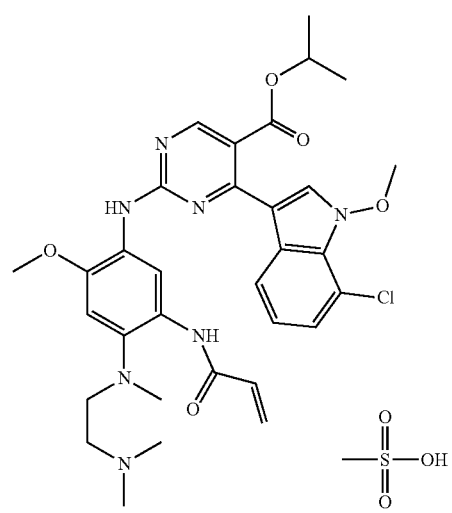

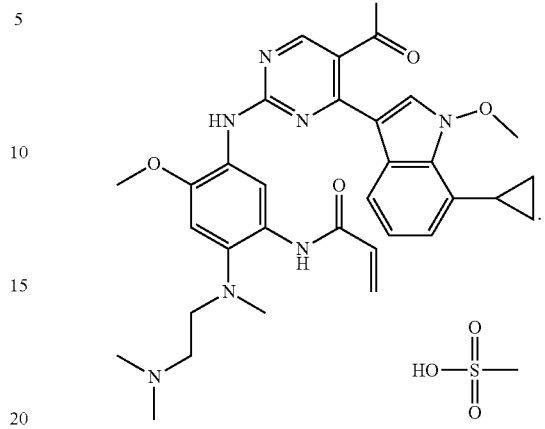

The present disclosure also provides a pharmaceutical composition comprising a therapeutically effective amount of the compound or the pharmaceutically acceptable salt thereof as the active ingredient and a pharmaceutically acceptable carrier.

The present disclosure also provides a use of the compound or the pharmaceutically acceptable salt thereof or the pharmaceutical composition in the manufacture of a medicament for diseases related to EGFR or ERBB2.

The present disclosure also provides a use of the compound or the pharmaceutically acceptable salt thereof or the pharmaceutical composition in the manufacture of a medicament for the treatment of cancer.

TECHNICAL EFFECT

The compounds of the present disclosure show better activity against EGFR and ERBB2 exon 20 insertion mutation, and may provide more effective treatment for diseases caused by abnormality of epidermal growth factor receptor enzyme.

Definition and Description

Unless otherwise specified, the following terms and phrases when used herein have the following meanings. A specific term or phrase should not be considered indefinite or unclear in the absence of a particular definition, but should be understood in the ordinary sense. When a trading name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

Unless otherwise specified, the term "effective amount" or "therapeutically effective amount" refers to an amount that is nontoxic but achieves the desired effect. The determination of the effective amount varies from person to person, depends on the age and general condition of the recipient, and also depends on the specific active substance, and the appropriate effective amount in individual cases can be determined by those skilled in the art based on routine experiments.

Unless otherwise specified, the term "$C_{1-3}$ alkyl" refers to a linear or branched saturated hydrocarbon group containing 1 to 3 carbon atoms. The $C_{1-3}$ alkyl group includes $C_{1-2}$ and $C_{2-3}$ alkyl groups and the like; it can be monovalent (such as methyl), divalent (such as methylene) or multivalent (such as methine). Examples of $C_{1-3}$ alkyl include but are not limited to methyl (Me), ethyl (Et), propyl (including n- and isopropyl) and the like.

The solvents used in the present disclosure are commercially available.

The following abbreviations are used in the present disclosure: DMF refers to N,N-dimethylformamide; TsOH.H$_2$O refers top-toluenesulfonic acid monohydrate; EDCI refers to 1-ethyl-3-(3-dimethylpropylamino)carbodiimide; DBU refers to 1,8-diazabicycloundec-7-ene; DIPEA refers to N,N-diisopropylethylamine; NaH refers to sodium hydrogen; EtONa refers to sodium ethoxide; m-CPBA refers to m-chloroperoxybenzoic acid; DCM refers to dichloromethane; NH$_4$Cl refers to ammonium chloride; NaOH refers to sodium hydroxide; DMF-DMA refers to N,N-dimethylformamide dimethyl acetal; MgCl$_2$ refers to magnesium chloride; CDI refers to carbonyl diimidazole; THF refers to tetrahydrofuran; NaH$_2$PO$_4$ refers to potassium dihydrogen phosphate; t-BuOH refers to tert-butanol; POCl$_3$ refers to phosphorus trichloroxide; NaClO$_2$ refers to sodium chlorite; TOMAC refers to trioctyl methyl ammonium chloride; MTBE refers to methyl tert-butyl ether.

The filler used in the column chromatography separation of the present disclosure are silica gel without special description; the filler used in the thin layer chromatography separation of the present disclosure is silica gel without special description.

The compounds of the present disclosure are named according to the conventional naming principles in the art or by ChemDraw® software, and the commercially available compounds use the supplier catalog names.

DETAILED DESCRIPTION OF THE PREFERRED EMBODIMENT

Figure 1:
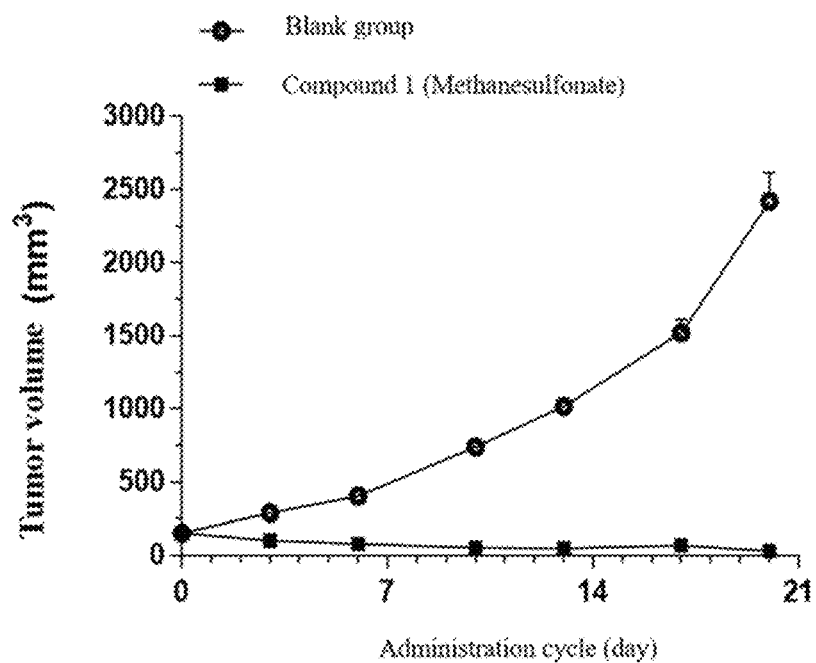
FIG. 1 shows the tumor growth curve of human lung cancer NCI-H1975 mice subcutaneous xenograft tumor model.

The present disclosure is described in detail by the embodiments below, but it does not mean that there are any adverse restrictions on the present disclosure. The compounds of the present disclosure can be prepared by a variety of synthetic methods known to those skilled in the art, including the specific embodiments listed below, embodiments resulting from their combination with other chemical synthesis methods, and equivalent substitutions known to those skilled in the art, preferred embodiments including, but not limited to, embodiments of the present disclosure. It will be apparent to those skilled in the art that various variations and improvements can be made to specific embodiments of the present disclosure without departing from the spirit and scope of the present disclosure.

Embodiment 1

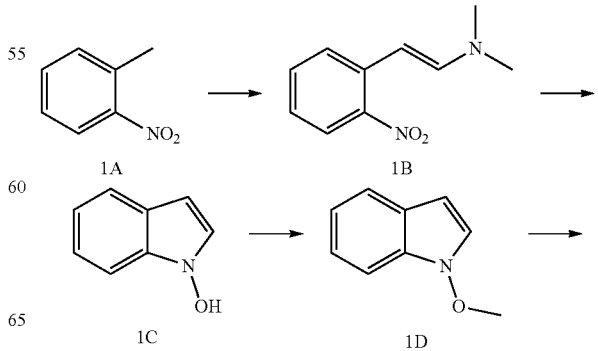

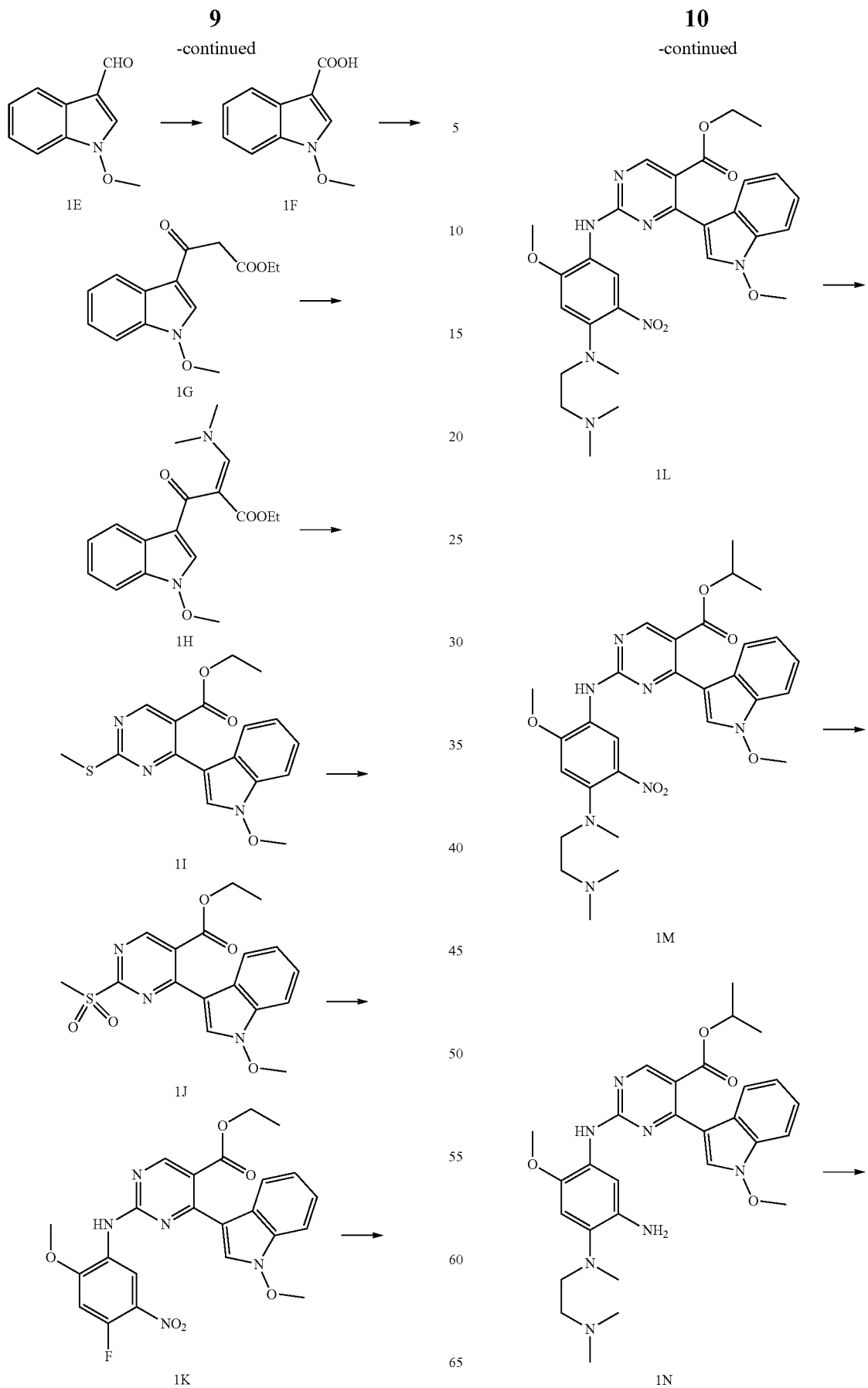

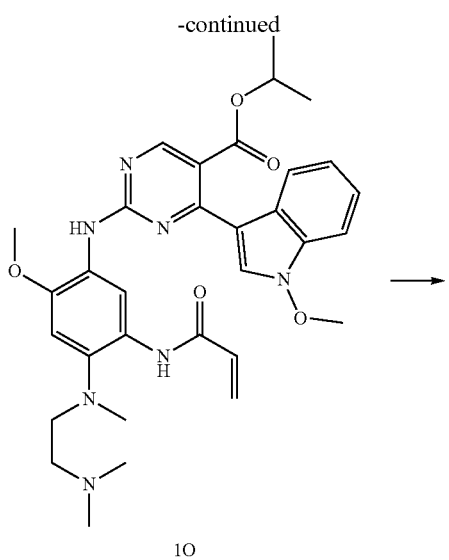

Compound 1

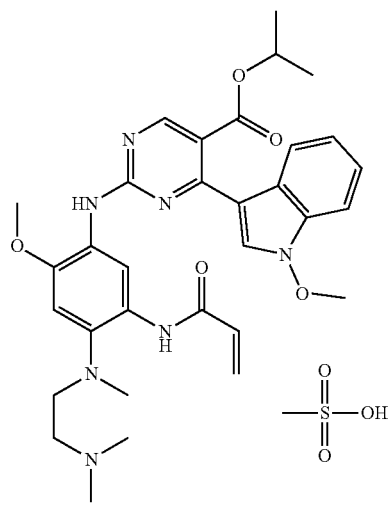

Compound 1B

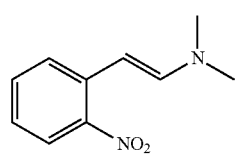

To a solution of compound 1A (12.3 g, 89.69 mmol) in DMF (100 mL) were added DBU (1.37 g, 8.97 mmol) and DMF-DMA (26.91 g, 225.83 mmol). The mixture was stirred at 120-130° C. for 16 hours, and the reaction was completed. The reaction solution was concentrated to obtain the title compound.

Compound 1C

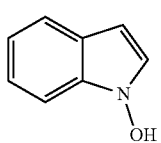

To a solution of compound 1B (17.24 g, 89.69 mmol) in MTBE (300 mL) were added zinc powder (70 g, 1.07 mol) and aqueous solution (60 mL) of ammonium chloride (19 g, 355.20 mol) in batches under nitrogen protection. The mixture was stirred at 20-30° C. for 4 hours. The reaction was completed. The reaction solution was filtered under reduced pressure, and the filter cake was washed with MTBE (50 mL), then the filtrates were combined and washed with saturated sodium bicarbonate aqueous solution (50 mL×2) and dried over anhydrous sodium sulfate to obtain a solution of the title compound, which can be directly used in the next reaction step. LCMS (ESI): m/z: 134.6 [M+1].

Compound 1D

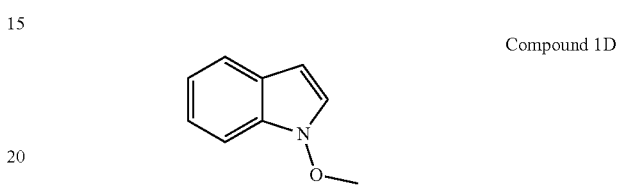

To a solution of compound 1C (11.94 g, 89.68 mmol) in MTBE (350 mL) were added iodomethane (68.40 g, 481.9 mmol), NaOH aqueous solution (2.5 M, 300 mL) and TOMAC (1.81 g, 4.48 mmol). The mixture was stirred at 20-30° C. for 12 hours, and the reaction was completed. The phases of the reaction solution were separated, and the lower aqueous phase was extracted with ethyl acetate (100 mL), then the organic phases were combined, dried with anhydrous sodium sulfate, filtered and concentrated. The crude product was separated and purified by silica gel column chromatography (petroleum ether:ethyl acetate=80:1, v/v) to obtain the title compound. $^1$H NMR (400 MHz, CDCl$_3$-d) δ=7.62-7.57 (m, 1H), 7.45 (dd, J=0.9, 8.2 Hz, 1H), 7.27 (d, J=3.4 Hz, 1H), 7.26-7.23 (m, 1H), 7.11 (ddd, J=1.0, 7.0, 7.9 Hz, 1H), 6.36 (dd, J=0.7, 3.4 Hz, 1H), 4.09 (s, 3H). LCMS (ESI) m/z: 148.6 [M+1].

Compound 1E

Under nitrogen protection, POCl$_3$ (4.7 g, 30.65 mmol, 2.85 mL) was slowly added dropwise to DMF (20 mL) solution at 0-10° C., and after stirring for 15 minutes, compound 1D (2.3 g, 15.63 mmol) was added, and the mixture was stirred at 20-30° C. for 2 hours. The reaction solution was quenched by adding 15% NaOH (20 mL) aqueous solution, and the reaction solution was extracted by adding ethyl acetate (20 mL×3). The combined organic phases were dried with anhydrous sodium sulfate, filtered and concentrated. The crude product was separated and purified by silica gel column chromatography (petroleum ether:ethyl acetate=10:1 v/v) to obtain the title compound. $^1$H NMR (400 MHz, CDCl$_3$-d) δ=9.99 (s, 1H), 8.36-8.31 (m, 1H), 7.91 (s, 1H), 7.53-7.48 (m, 1H), 7.40 (dt, J=1.3, 7.6 Hz, 1H), 7.38-7.33 (m, 1H), 4.21 (s, 3H).

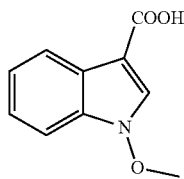

Compound 1F

To a solution of compound 1E (2.6 g, 14.84 mmol) in t-BuOH (120 mL) and 2-methyl-2-butene (120 mL) was added aqueous solution (150 mL) of NaClO₂ (26.85 g, 296.83 mmol) and NaH₂PO₄ (26.71 g, 222.62 mmol) in batches at 0° C., and the mixture was stirred at 20-30° C. for 24 hours. The reaction solution was extracted by adding ethyl acetate (300 mL), and the organic phase was dried with anhydrous sodium sulfate, filtered, and the filtrate was concentrated to obtain the title compound. ¹H NMR (400 MHz, CDCl₃-d) δ=8.18-8.14 (m, 1H), 7.99 (s, 1H), 7.45-7.39 (m, 1H), 7.26 (d, J=1.1, 7.3 Hz, 2H), 4.11 (s, 3H). LCMS (ESI) m/z: 192.5 [M+1].

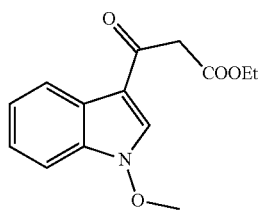

Compound 1G

Compound 1F (2.8 g, 14.65 mmol) and CDI (3.56 g, 21.97 mmol) were dissolved in THF (50 mL) and the mixture was stirred at 20° C. for 2 hours. To the mixture were added the potassium salt of monoethyl malonate (3.74 g, 21.97 mmol) and MgCl₂ (2.79 g, 29.29 mmol); and the reaction solution was stirred at 20-30° C. for 18 hours. Ethyl acetate (60 mL) was added to the reaction mixture, and the reaction solution was washed with water (50 mL), then the aqueous phase was extracted with ethyl acetate (50 mL), and the organic phases were combined, dried over anhydrous sodium sulfate, filtered and concentrated. The crude product was purified by silica gel column chromatography (petroleum ether:ethyl acetate=10:1 v/v) to obtain the title compound. ¹H NMR (400 MHz, CDCl₃-d) δ=8.33-8.28 (m, 1H), 7.92 (s, 1H), 7.42-7.38 (m, 1H), 7.27 (dtd, J=1.2, 7.3, 16.3 Hz, 2H), 4.18-4.12 (m, 2H), 4.11 (s, 3H), 3.78 (s, 2H), 1.20 (t, J=7.2 Hz, 3H). LCMS (ESI) m/z: 262.1 [M+1].

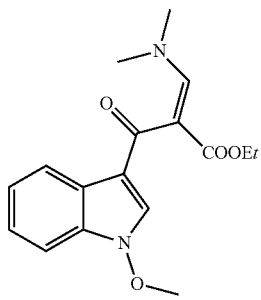

Compound 1H

Compound 1G (0.5 g, 1.91 mmol) was added to DMF-DMA (0.26 g, 2.18 mmol) and the reaction solution was stirred at 80-90° C. for 1 hour. The reaction solution was concentrated to obtain the title compound. The crude product can be used directly in the next reaction step.

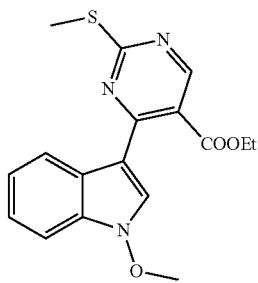

Compound 1I

Compound 1H (605 mg, 1.91 mmol) was dissolved in ethanol (6 mL), then EtONa (0.27 g, 3.97 mmol) and S-methylisothiourea sulfate (300 mg, 1.08 mmol) were added slowly, the mixture was stirred at 30° C. for 12 hours. The reaction solution was concentrated, and ethyl acetate (30 mL) was added to the mixture, then the reaction solution was washed with saturated saline (20 mL), and the organic phase was dried with anhydrous sodium sulfate, filtered and concentrated. The crude product was separated and purified by silica gel preparative thin layer chromatography plates (petroleum ether:ethyl acetate=5:1) to obtain the title compound. ¹H NMR (400 MHz, CDCl₃-d) δ=8.86 (s, 1H), 8.18-8.14 (m, 1H), 8.09 (s, 1H), 7.51 (td, J=0.9, 8.1 Hz, 1H), 7.37-7.32 (m, 1H), 7.29-7.24 (m, 1H), 4.31 (q, J=7.1 Hz, 2H), 4.19 (s, 3H), 2.70 (s, 3H), 1.23 (t, J=7.1 Hz, 3H). LCMS (ESI) m/z: 344.2 [M+1].

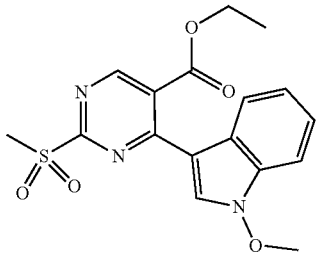

Compound 1J

Compound 1I (180 mg, 0.524 mmol) was dissolved in DCM (5 mL), and m-CPBA (226 mg, 1.05 mmol, 80% purity) was added to the mixture; and the reaction solution was stirred at 25° C. for 5 hours. The reaction solution was quenched by adding saturated sodium sulfite solution (20 mL), extracted by adding DCM (50 mL), and the organic phase was dried with anhydrous sodium sulfate, filtered and concentrated to obtain the title compound. LCMS (ESI) m/z: 376.0 [M+1].

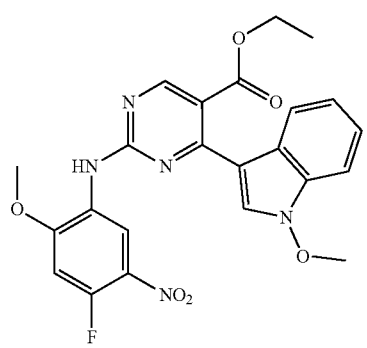

Compound 1K

To a solution of compound 1J (300 mg, 0.8 μmol) and 4-fluoro-2-methoxy-5-nitro-aniline (179 mg, 0.961 mmol) in dioxane (10 mL) was added TsOH.H$_2$O (456 mg, 2.40 mmol), and the reaction solution was stirred at 100° C. for 16 hours. The reaction mixture was extracted by adding ethyl acetate (50 mL), and the organic phase was washed with saturated sodium bicarbonate (30 mL), then the organic phase was separated and dried with anhydrous sodium sulfate, filtered and concentrated to obtain a crude product, which was separated and purified by silica gel preparative thin layer chromatography (petroleum ether:ethyl acetate=2: 1) to obtain the title compound. LCMS (ESI) m/z: 482.1 [M+1].

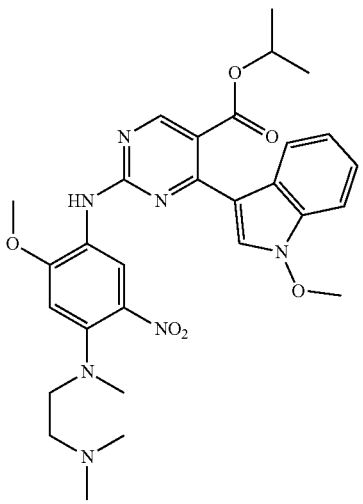

Compound 1M

NaH (47 mg, 1.18 mmol, 60% purity) was added to isopropanol (1 mL) under nitrogen protection, and the reaction solution was stirred at 25° C. for 15 min. A solution of compound 1L (130 mg, 230.66 μmol) in THF (0.5 mL) was added dropwise to the above solution. The reaction solution was stirred at 80° C. for 1 hour. The reaction solution was quenched by adding purified water (30 mL), and the aqueous phase was extracted with DCM (60 mL), then the organic phase was dried and concentrated to obtain the title compound. LCMS (ESI) m/z: 578.0 [M+1].

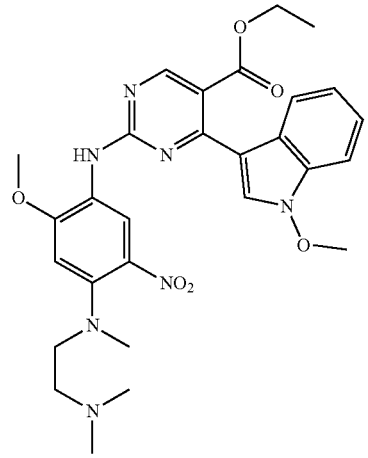

Compound 1L

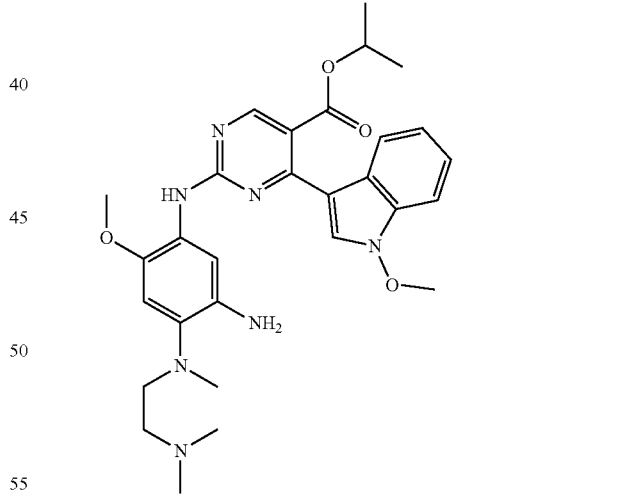

Compound 1N

To a solution of compound 1K (150 mg, 311.57 μmol) in DMF (2 mL) were added N,N,N-trimethylethylenediamine (58 mg, 567.6 μmol) and DIPEA (82.14 mg, 0.635 mmol). The reaction solution was stirred at 100° C. for 0.5 hours. The reaction solution was cooled to room temperature, then purified water (20 mL) was added, and a solid was precipitated from the solution, then the mixture was filtered under reduced pressure, and the filter cake was dried to obtain the title compound. LCMS (ESI) m/z: 564.2 [M+1].

To a solution of compound 1M (89 mg, 0.154 mmol) in ethanol (3 mL) and purified water (1 mL) were added zinc powder (101 mg, 1.54 mmol) and NH$_4$Cl (83 mg, 1.55 mmol) under nitrogen protection, and the reaction solution was stirred at 25° C. for 1 hour. The reaction solution was filtered under reduced pressure, and the filtrate was added with purified water (20 mL), then the filtrate was extracted by adding DCM (45 mL), and the organic phase was dried and concentrated to obtain the title compound. LCMS (ESI) m/z: 548.2 [M+1].

Compound 1O

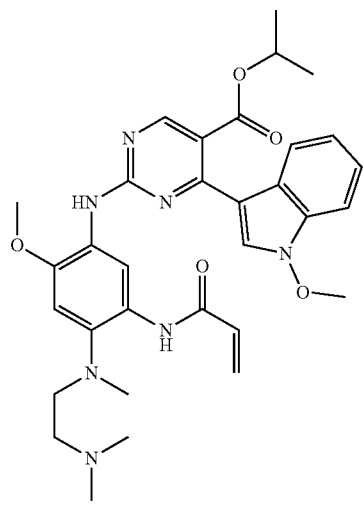

To a solution of compound 1O (84 mg, 153,38 μmol) and acrylic acid (17 mg, 0.236 mmol) in dichloromethane (2 mL) were added EDCI (44 mg, 229 μmol) and DIPEA (40 mg, 309 μmol), and the reaction solution was stirred at 25° C. for 1 hour. Water (10 mL) was added to the reaction mixture, then the mixture was extracted with DCM (15 mL×2), and the organic phase was separated and dried with anhydrous sodium sulfate, filtered and concentrated to obtain a crude product, which was separated and purified by silica gel preparative thin layer chromatography plate (DCM:MeOH=10:1) to obtain the title compound. $^1$H NMR (400 MHz, Methanol-d$_4$) δ=9.31-9.13 (m, 1H), 8.85-8.76 (m, 1H), 8.47 (br d, J=5.6 Hz, 1H), 7.73-7.63 (m, 1H), 7.51 (d, J=8.3 Hz, 1H), 7.31-7.23 (m, 1H), 7.17-7.08 (m, 1H), 6.99 (s, 1H), 6.66-6.34 (m, 2H), 5.97-5.74 (m, 1H), 5.04-4.96 (m, 1H), 4.59 (br s, 3H), 4.20 (s, 3H), 3.95 (s, 3H), 3.15-3.05 (m, 2H), 2.71 (s, 3H), 2.58-2.45 (m, 2H), 2.35 (br s, 3H), 1.08 (d, J=6.1 Hz, 6H). LCMS (ESI) m/z: 602.3 [M+1].

Compound 1

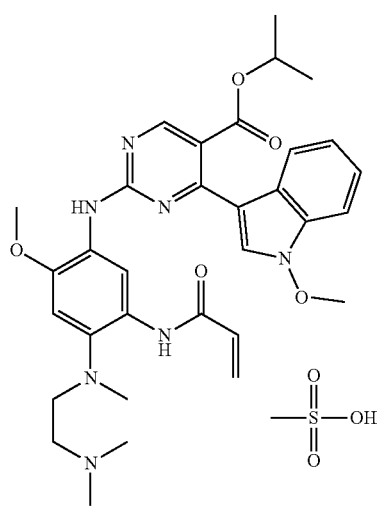

To a solution of compound 1O (15 mg, 24.93 μmol) in acetonitrile (0.5 mL) and water (10 mL) was added methanesulfonic acid (2.40 mg, 24.93 μmol). The mixture was freeze-dried to obtain the title compound. $^1$H NMR (400 MHz, Methanol-d$_4$) δ=9.18-8.95 (m, 1H), 8.79 (s, 1H), 8.44-8.29 (m, 1H), 7.73 (br d, J=7.3 Hz, 1H), 7.51 (d, J=8.3 Hz, 1H), 7.26 (t, J=7.6 Hz, 1H), 7.17-7.08 (m, 1H), 6.97 (s, 1H), 6.58-6.31 (m, 2H), 5.83 (dd, J=2.1, 9.6 Hz, 1H), 5.00 (quin, J=6.3 Hz, 1H), 4.57 (br s, 3H), 4.19 (s, 3H), 3.96 (s, 3H), 3.25-3.10 (m, 2H), 2.77-2.62 (m, 6H), 2.48 (br s, 5H), 1.09 (d, J=6.3 Hz, 6H). LCMS (ESI) m/z: 602.3 [M+1].

Embodiment 2

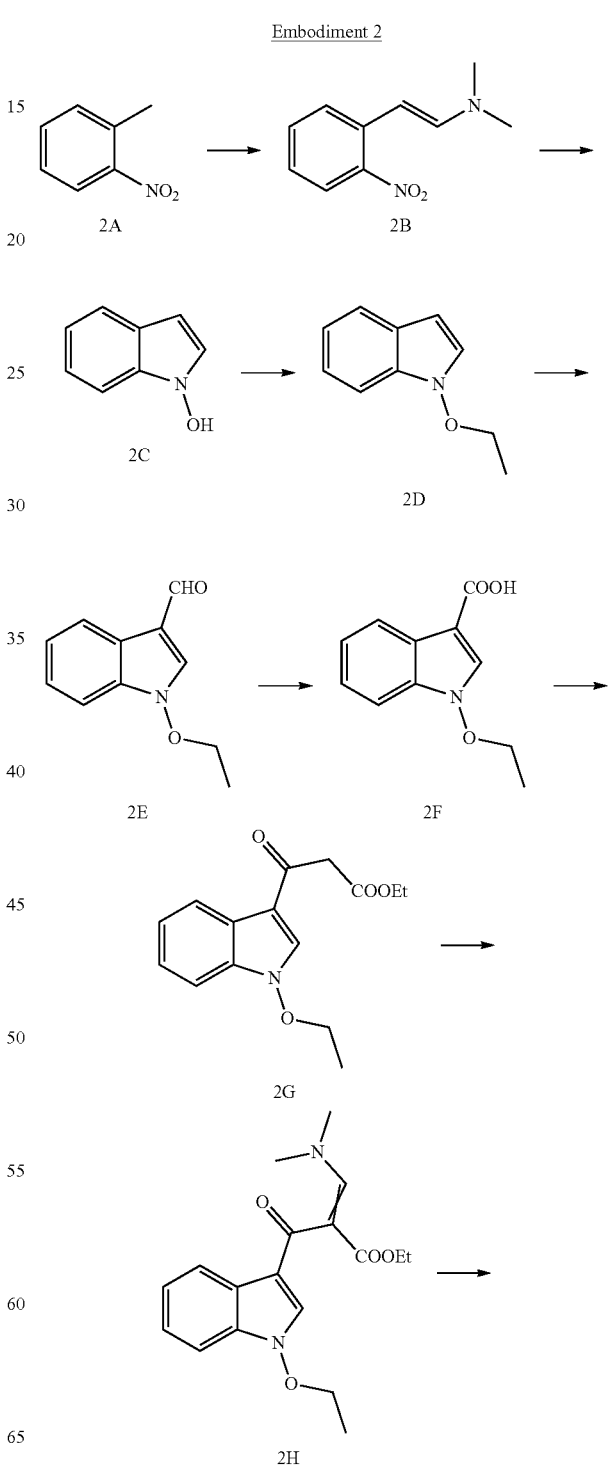

19
-continued
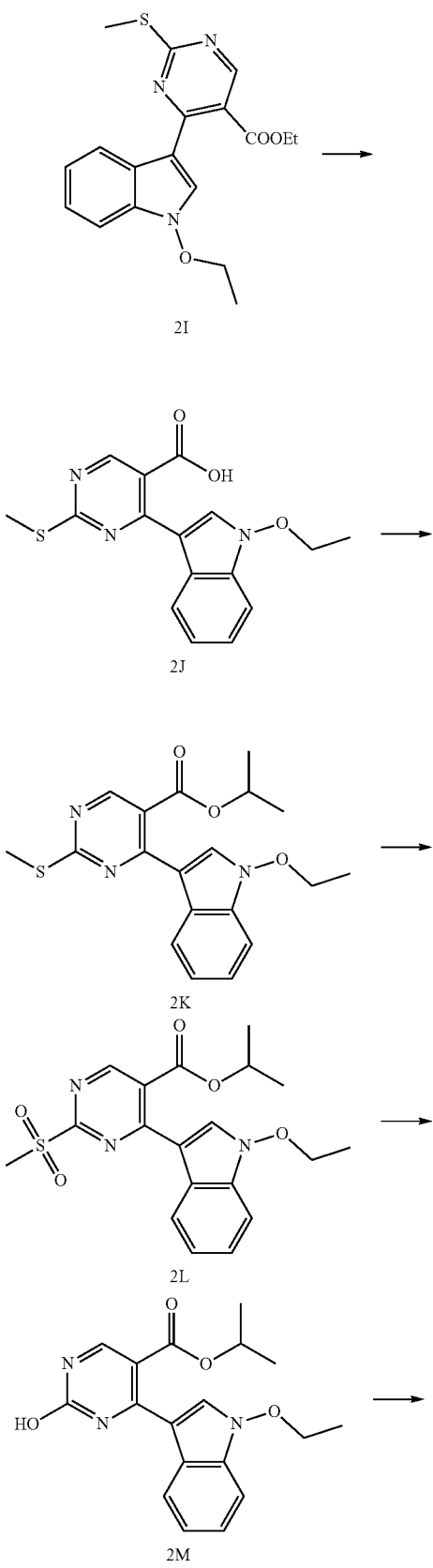
2I
2J
2K
2L
2M
20
-continued
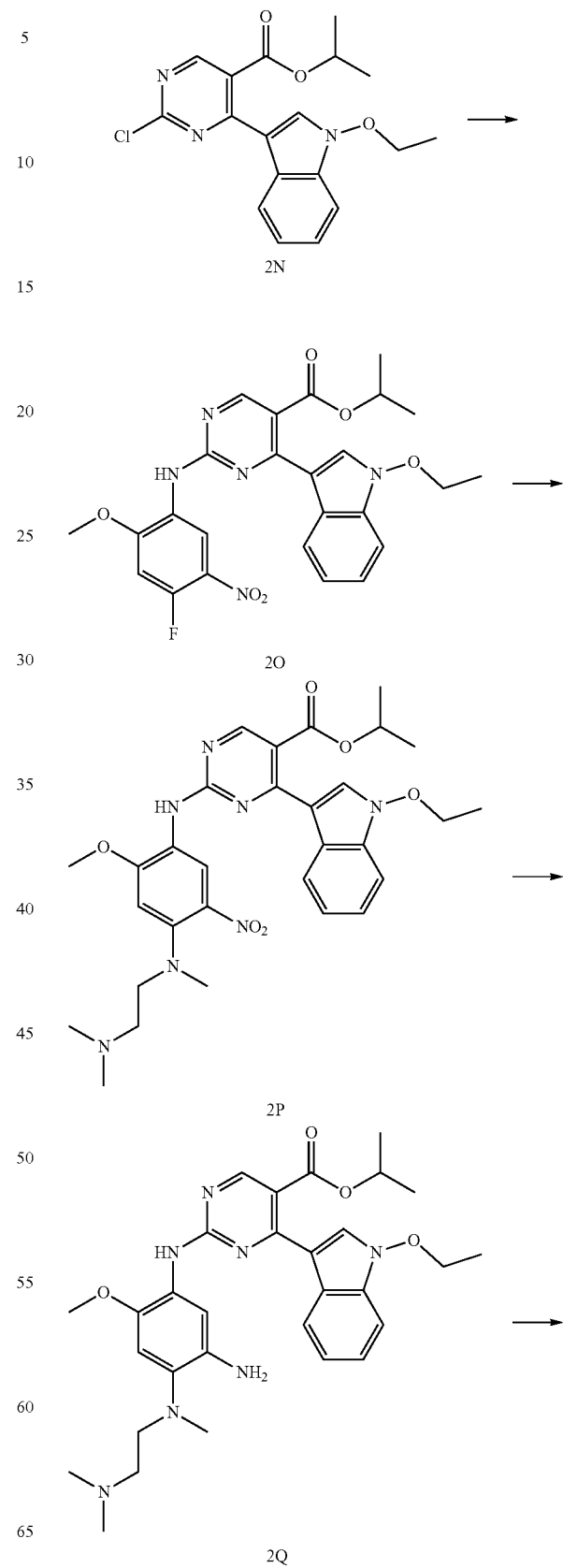
2N
2O
2P
2Q

-continued

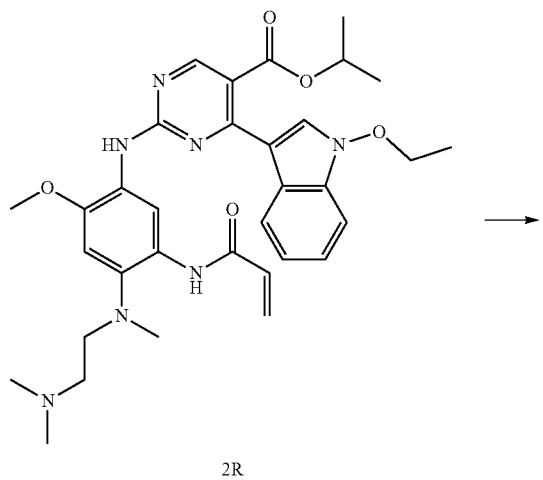

2R

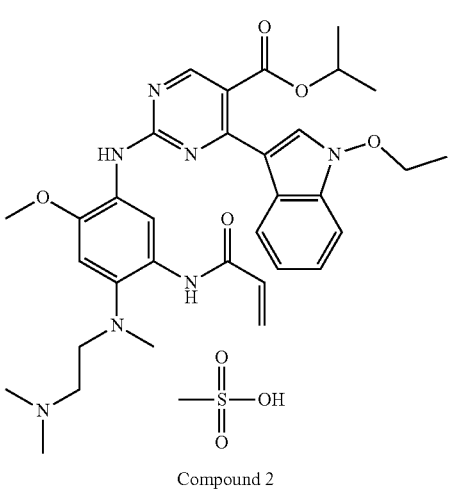

Compound 2

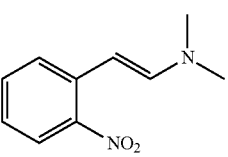

Compound 2B

This compound was prepared according to the method of compound 1B in Embodiment 1, replacing compound 1A with compound 2A.

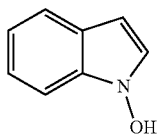

Compound 2C

This compound was prepared according to the method of compound 1C in Embodiment 1, replacing compound 1B with compound 2B.

Compound 2D

To a solution of compound 2C (11.08 g, 83.22 mmol) in 2-MeTHF (400 mL) were added ethyl iodide (65.13 g, 417.59 mmol), NaOH aqueous solution (2 M, 400 mL) and TOMAC (1.67 g, 4.14 mmol). The mixture was stirred at 20-30° C. for 12 hours. The reaction was completed. The phases of the reaction solution were separated and the lower aqueous phase was extracted with ethyl acetate (200 mL×2), then the organic phases were combined, dried with anhydrous sodium sulfate, filtered and concentrated. The crude product was purified by silica gel column chromatography (petroleum ether:ethyl acetate=1:0, v/v) to obtain the title compound. $^1$H NMR (400 MHz, CDCl$_3$-d) δ=7.51 (td, J=0.9, 8.0 Hz, 1H), 7.35 (dd, J=0.9, 8.2 Hz, 1H), 7.18-7.13 (m, 2H), 7.02 (ddd, J=1.1, 7.0, 8.0 Hz, 1H), 6.27 (dd, J=1.0, 3.4 Hz, 1H), 4.24 (q, J=7.1 Hz, 2H), 1.33 (t, J=7.1 Hz, 3H). LCMS (ESI) m/z: 162.5 [M+1].

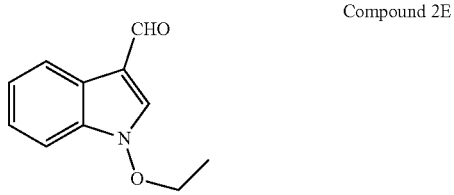

Compound 2E

This compound was prepared according to the method of compound 1E in Embodiment 1, replacing compound 1D with compound 2D. $^1$H NMR (400 MHz, CDCl$_3$-d) δ=9.89 (s, 1H), 8.26-8.21 (m, 1H), 7.79 (s, 1H), 7.41-7.37 (m, 1H), 7.32-7.27 (m, 1H), 7.27-7.23 (m, 1H), 4.32 (q, J=7.0 Hz, 2H), 1.38 (t, J=7.1 Hz, 3H). LCMS (ESI) m/z: 190.1 [M+1].

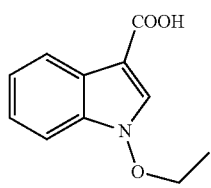

Compound 2F

This compound was prepared according to the method of compound 1F in Embodiment 1, replacing compound 1E with compound 2E. $^1$H NMR (400 MHz, CDCl$_3$-d) δ=8.28-8.23 (m, 1H), 8.07 (s, 1H), 7.52-7.48 (m, 1H), 7.39-7.31 (m, 2H), 4.41 (q, J=7.1 Hz, 2H), 1.47 (t, J=7.1 Hz, 3H). LCMS (ESI) m/z: 205.8 [M+1].

Compound 2G

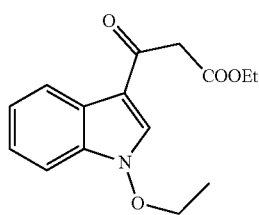

This compound was prepared according to the method of compound 1G in Embodiment 1, replacing compound 1F with compound 2F. ¹H NMR (400 MHz, CDCl₃-d) δ=8.32-8.29 (m, 1H), 7.90 (s, 1H), 7.40-7.36 (m, 1H), 7.30-7.22 (m, 2H), 4.32 (q, J=6.9 Hz, 2H), 4.14 (q, J=7.1 Hz, 2H), 3.78 (s, 2H), 1.38 (t, J=7.1 Hz, 3H), 1.20 (t, J=7.1 Hz, 3H). LCMS (ESI) m/z: 276.4 [M+1].

Compound 2H

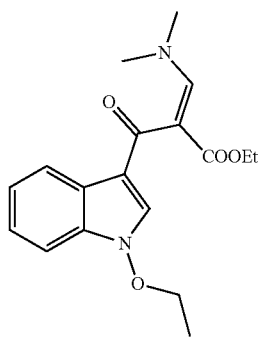

This compound was prepared according to the method of compound 1H in Embodiment 1, replacing compound 1G with compound 2G.

Compound 2I

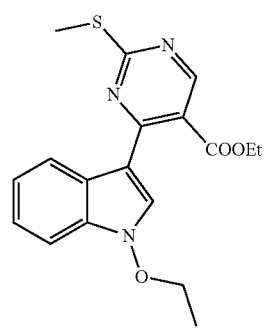

This compound was prepared according to the method of compound 1I in Embodiment 1, replacing compound 1H with compound 2H. ¹H NMR (400 MHz, CDCl₃-d) δ=8.76 (s, 1H), 8.08 (d, J=8.0 Hz, 1H), 7.97 (s, 1H), 7.40 (d, J=8.0 Hz, 1H), 7.27-7.21 (m, 1H), 7.19-7.14 (m, 1H), 4.32 (q, J=7.1 Hz, 2H), 4.21 (q, J=7.1 Hz, 2H), 2.61 (s, 3H), 1.38 (t, J=7.0 Hz, 3H), 1.14 (t, J=7.1 Hz, 3H). LCMS (ESI) m/z: 358.2 [M+1].

Compoudn 2J

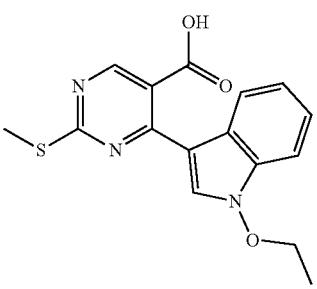

Compound 2I (0.74 g, 2.07 mmol) was dissolved in ethanol (8 mL) and sodium hydroxide aqueous solution (2 M, 4 mL) was added. The reaction system was stirred for 1 hour at 20-30° C. LCMS was used to monitor the end of the reaction. The reaction solution was adjusted to pH 3-4 with hydrochloric acid aqueous solution (2 M), then extracted with ethyl acetate (10 mL×3). The combined organic phases were dried with anhydrous sodium sulfate and concentrated under reduced pressure to obtain the title compound. ¹H NMR (400 MHz, CDCl₃-d) δ=8.90 (s, 1H), 8.15 (d, J=8.0 Hz, 1H), 8.03 (s, 1H), 7.42-7.38 (m, 1H), 7.24 (dt, J=1.1, 7.6 Hz, 1H), 7.19-7.16 (m, 1H), 4.30 (q, J=7.1 Hz, 2H), 2.62 (s, 3H), 1.36 (t, J=7.1 Hz, 3H). LCMS (ESI) m/z: 330.3 [M+1].

Compound 2K

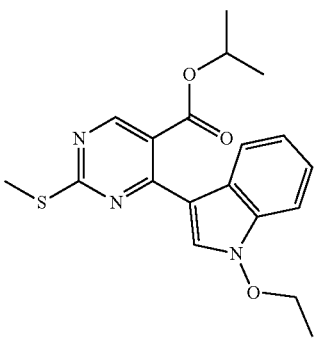

Compound 2J (0.66 g, 2.00 mmol) and 2-iodopropane (1.70 g, 10.00 mmol) were dissolved in N,N-dimethylformamide (7 mL), and cesium carbonate (1.31 g, 4.01 mmol) was added. The mixture was stirred for 1 hour at an internal temperature of 40-50° C. Ethyl acetate (30 mL) was added to the reaction solution, and the mixture was filtered. The filtrate was washed with saturated NaCl aqueous solution (7 mL×1). The washed aqueous phase was extracted with ethyl acetate (7 mL×2). The combined organic phases were dried with anhydrous sodium sulfate and concentrated under reduced pressure to obtain the title compound. ¹H NMR (400 MHz, CDCl₃-d) δ=8.73 (s, 1H), 8.06 (d, J=8.1 Hz, 1H), 7.97 (s, 1H), 7.40 (d, J=8.1 Hz, 1H), 7.26-7.21 (m, 1H), 7.19-7.13 (m, 1H), 5.07 (spt, J=6.2 Hz, 1H), 4.31 (q, J=7.1

Hz, 2H), 2.60 (s, 3H), 1.38 (t, J=7.1 Hz, 3H), 1.14 (d, J=6.4 Hz, 6H). LCMS (ESI) m/z: 372.3 [M+1].

4.40-4.28 (m, 2H), 1.34 (t, J=7.0 Hz, 3H), 0.96 (d, J=6.3 Hz, 6H).

Compound 2L

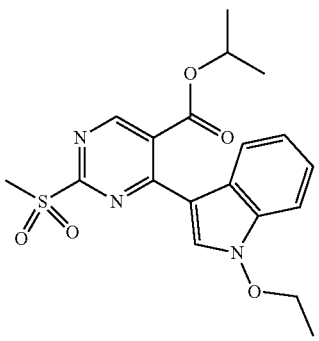

This compound was prepared according to the method of compound 1J in Embodiment 1, replacing compound 1I with compound 2K. $^1$H NMR (400 MHz, CDCl$_3$-d) δ=9.00 (s, 1H), 8.40-8.35 (m, 1H), 8.22 (s, 1H), 7.54-7.49 (m, 1H), 7.41-7.32 (m, 2H), 5.29 (m, 1H), 4.43 (q, J=7.1 Hz, 2H), 3.43 (s, 3H), 1.48 (t, J=7.1 Hz, 3H), 1.32 (d, J=6.4 Hz, 6H). LCMS (ESI) m/z: 404.2 [M+1].

Compound 2M

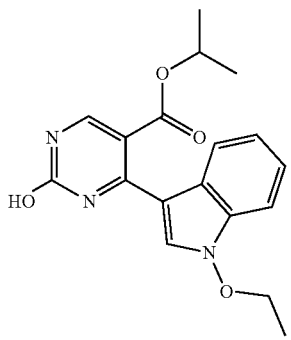

Compound 2L (760 mg, 1.88 mmol) was dissolved in tetrahydrofuran (10 mL), and sodium tert-butoxide (905.17 mg, 9.42 mmol) was added and the reaction was stirred for 1 hour at 25° C. The end of the reaction was monitor by LCMS. Water (20 mL) was added to the reaction solution and the mixture was extracted with dichloromethane (20 mL×3 times). The combined organic phases were washed with saturated saline (20 mL×2 times), the phases were separated, and the organic phase was dried with anhydrous sodium sulfate and filtered, and the filtrate was evaporated to dryness by rotary evaporation to obtain the title compound. $^1$H NMR (400 MHz, DMSO-d$_6$) δ=8.51 (s, 1H), 7.98 (s, 1H), 7.72 (d, J=8.0 Hz, 1H), 7.47 (d, J=8.2 Hz, 1H), 7.26-7.18 (m, 1H), 7.14-7.03 (m, 1H), 4.82-4.71 (m, 1H), Compound 2N

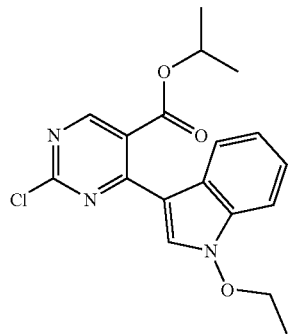

Compound 2M (640 mg, 1.87 mmol) was added to POCl$_3$ (13.20 g, 86.09 mmol) for 1 hour at 80° C. with stirring. The reaction solution was concentrated under reduced pressure and the remaining residue was added with ethyl acetate (20 mL) and saturated sodium bicarbonate aqueous solution (10 mL) at 0° C. The phases were separated, and the organic phase was washed with saturated saline (20 mL×1), then the phases were separated. The organic phase was dried and concentrated to obtain the title compound. $^1$H NMR (400 MHz, DMSO-d$_6$) δ=8.91 (s, 1H), 8.35 (s, 1H), 8.12 (d, J=8.0 Hz, 1H), 7.67-7.55 (m, 1H), 7.39-7.33 (m, 1H), 7.32-7.25 (m, 1H), 5.14 (spt, J=6.3 Hz, 1H), 4.42 (q, J=7.0 Hz, 2H), 1.35 (t, J=7.0 Hz, 3H), 1.21 (d, J=6.3 Hz, 6H).

Compound 2O

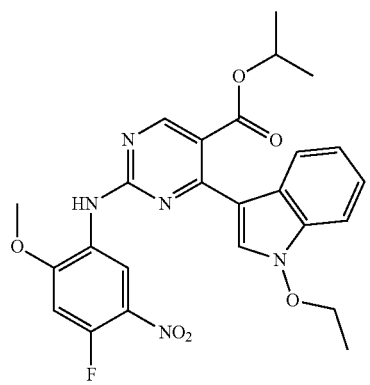

This compound was prepared according to the method of compound 1K in Embodiment 1, replacing compound 1J with compound 2N. $^1$H NMR (400 MHz, DMSO-d$_6$) δ=9.12 (s, 1H), 8.82 (d, J=8.4 Hz, 1H), 8.78 (s, 1H), 8.21 (s, 1H), 7.84 (br d, J=7.3 Hz, 1H), 7.60-7.49 (m, 1H), 7.41 (d, J=13.4 Hz, 1H), 7.33-7.25 (m, 1H), 7.10 (t, J=7.4 Hz, 1H), 5.10-4.95 (m, 1H), 4.40 (q, J=7.0 Hz, 2H), 3.99 (s, 3H), 1.38-1.34 (m, 3H), 1.15 (d, J=6.2 Hz, 6H).

Compound 2P

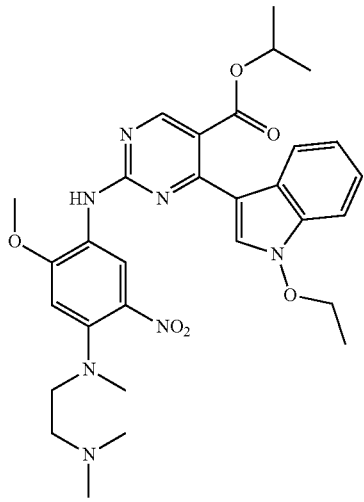

This compound was prepared according to the method of compound 1L in Embodiment 1, replacing compound 1K with compound 2O. $^1$H NMR (400 MHz, DMSO-d$_6$) δ=8.93 (s, 1H), 8.75-8.68 (m, 1H), 8.28 (s, 1H), 8.17 (s, 1H), 7.85 (br s, 1H), 7.55-7.49 (m, 1H), 7.25 (t, J=7.6 Hz, 1H), 7.07 (br d, J=7.8 Hz, 1H), 6.88-6.76 (m, 1H), 5.02 (td, J=6.3, 12.4 Hz, 1H), 4.41-4.35 (m, 2H), 3.94-3.89 (m, 3H), 3.30-3.27 (m, 2H), 2.86 (s, 3H), 2.48-2.47 (m, 2H), 2.15 (s, 6H), 1.36-1.32 (m, 3H), 1.18-1.14 (m, 6H).

Compound 2Q

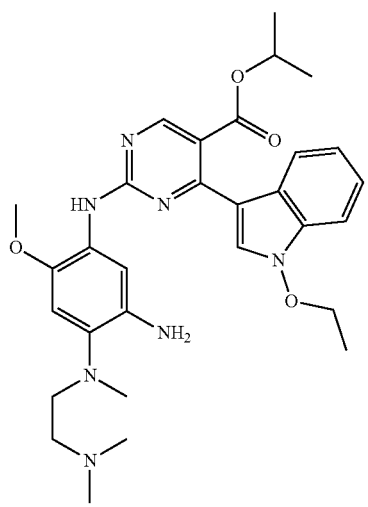

This compound was prepared according to the method of compound 1N in Embodiment 1, replacing compound 1M with compound 2P. $^1$H NMR (400 MHz, DMSO-d$_6$) δ=8.74-8.65 (m, 2H), 8.01-7.87 (m, 2H), 7.51 (d, J=8.2 Hz, 1H), 7.25 (br t, J=7.4 Hz, 1H), 7.18-7.06 (m, 2H), 6.80 (br s, 1H), 5.76 (s, 2H), 5.01 (td, J=6.2, 12.4 Hz, 1H), 4.37 (q, J=7.0 Hz, 2H), 3.71 (s, 3H), 2.95-2.90 (m, 2H), 2.65 (s, 3H), 2.40 (br d, J=6.4 Hz, 2H), 2.20 (s, 6H), 1.34 (t, J=7.0 Hz, 3H), 1.15 (d, J=6.2 Hz, 6H).

Compound 2R

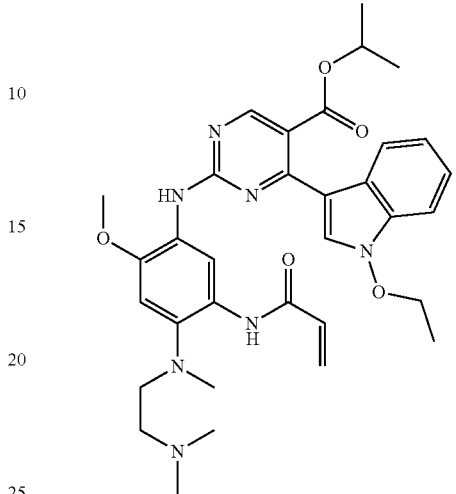

This compound was prepared according to the method of compound 1O in Embodiment 1, replacing compound 1N with compound 2Q. LCMS (ESI) m/z: 616.2 [M+1].

Compound 2

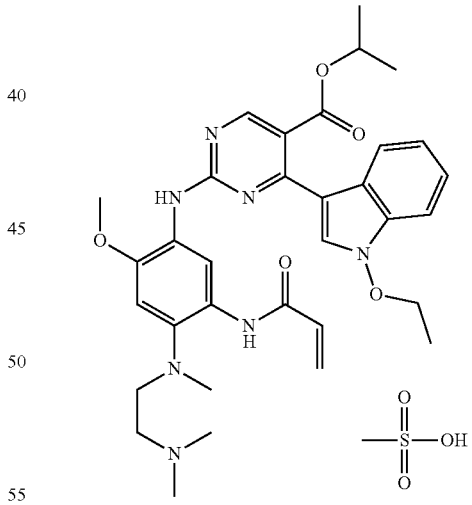

The present compound was prepared according to the method of compound 1 in Embodiment 1, replacing compound 1O with compound 2R to obtain the title compound. $^1$H NMR (400 MHz, Methanol-d$_4$) δ=8.80 (s, 1H), 8.56 (s, 1H), 8.11 (s, 1H), 7.90 (d, J=8.0 Hz, 1H), 7.50 (d, J=8.3 Hz, 1H), 7.25 (t, J=7.3 Hz, 1H), 7.16-7.08 (m, 1H), 6.96 (s, 1H), 6.50-6.41 (m, 2H), 5.93-5.76 (m, 1H), 5.06 (td, J=6.2, 12.5 Hz, 1H), 4.41 (q, J=7.0 Hz, 2H), 4.01 (s, 3H), 3.52-3.44 (m, 2H), 3.28-3.25 (m, 2H), 2.86 (s, 6H), 2.70 (d, J=3.0 Hz, 6H), 1.43 (t, J=7.0 Hz, 3H), 1.16 (d, J=6.3 Hz, 6H).

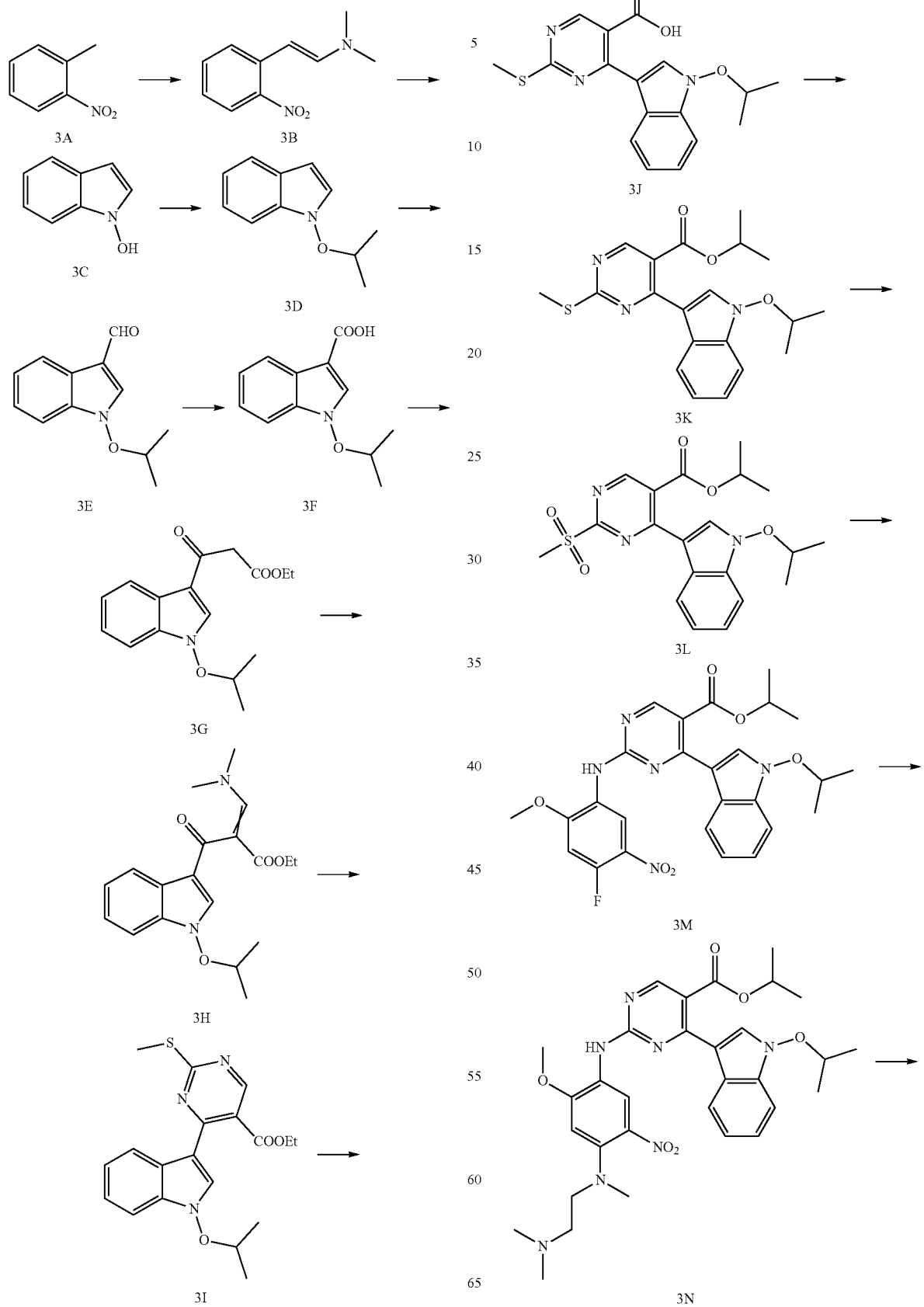

-continued

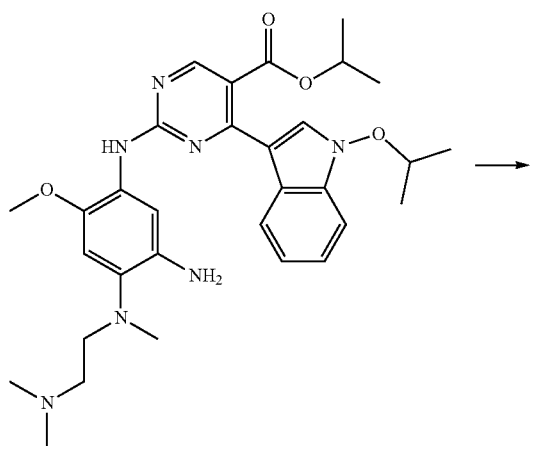

3O

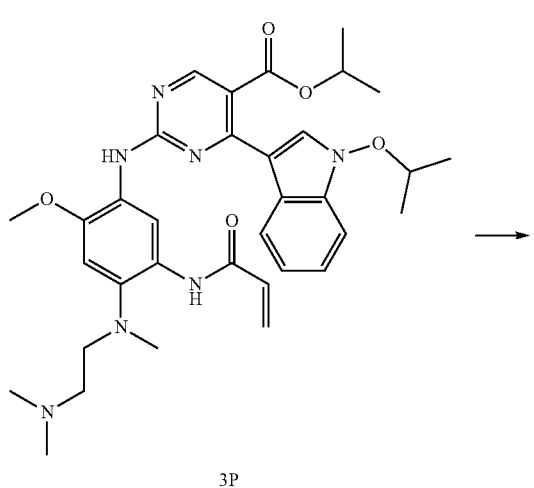

3P

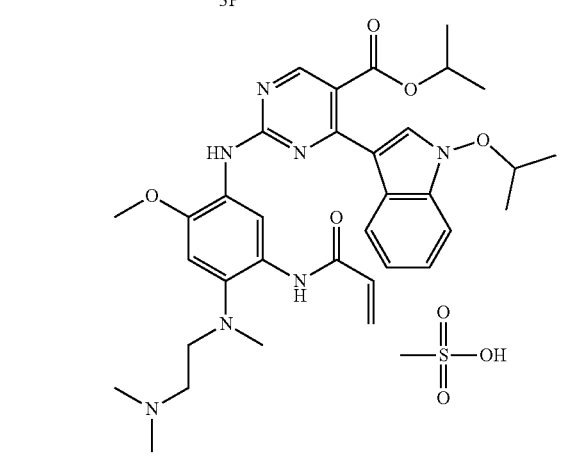

Compound 3

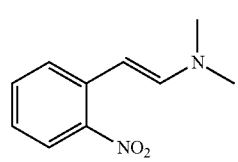

Compound 3B

This compound was prepared according to the method of compound 1B in Embodiment 1, replacing compound 1A with compound 3A.

Compound 3C

This compound was prepared according to the method of compound 1C in Embodiment 1, replacing compound 1B with compound 3B.

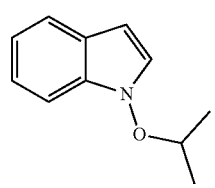

Compound 3D

To a solution of compound 3C (1.39 g, 10.44 mmol) in 2-MeTHF (50 mL) were added 2-iodopropane (8.50 g, 50 mmol), NaOH aqueous solution (2 M, 50 mL) and TOMAC (210 mg, 519.60 μmol). The mixture was stirred at 20-30° C. for 48 hours. The reaction was completed. The phases of the reaction solution were separated and the lower aqueous phase was extracted with ethyl acetate (20 mL×2), then the organic phases were combined, dried with anhydrous sodium sulfate, filtered and concentrated. The crude product was purified by silica gel column chromatography (petroleum ether:ethyl acetate=1:0, v/v) to obtain the title compound. $^1$H NMR (400 MHz, CDCl$_3$-d) δ=7.51 (d, J=7.8 Hz, 1H), 7.33 (dd, J=0.9, 8.2 Hz, 1H), 7.17-7.11 (m, 2H), 7.01 (dt, J=1.0, 7.6 Hz, 1H), 6.26 (dd, J=0.7, 3.4 Hz, 1H), 4.47 (spt, J=6.2 Hz, 1H), 1.29 (d, J=6.4 Hz, 6H). LCMS (ESI) m/z: 176.5 [M+1].

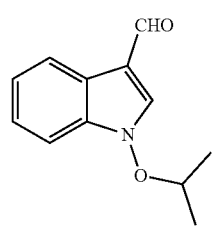

Compound 3E

This compound was prepared according to the method of compound 1E in Embodiment 1, replacing compound 1D with compound 3D. $^1$H NMR (400 MHz, CDCl$_3$-d) δ=9.99 (s, 1H), 8.32 (d, J=7.6 Hz, 1H), 7.85 (s, 1H), 7.50-7.45 (m, 1H), 7.41-7.31 (m, 2H), 4.65 (spt, J=6.2 Hz, 1H), 1.42 (d, J=6.1 Hz, 6H). LCMS (ESI) m/z: 204.5 [M+1].

Compound 3F

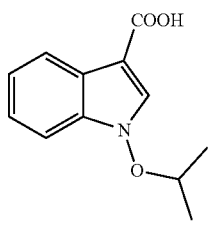

This compound was prepared according to the method of compound 1F in Embodiment 1, replacing compound 1E with compound 3E. $^1$H NMR (400 MHz, CDCl$_3$-d) δ=8.29-8.23 (m, 1H), 8.04 (s, 1H), 7.51-7.46 (m, 1H), 7.38-7.30 (m, 2H), 4.65 (spt, J=6.1 Hz, 1H), 1.42 (d, J=6.3 Hz, 6H). LCMS (ESI) m/z: 220.4 [M+1].

Compound 3G

This compound was prepared according to the method of compound 1G in Embodiment 1, replacing compound 1F with compound 3F. $^1$H NMR (400 MHz, CDCl$_3$-d) δ=8.42-8.37 (m, 1H), 7.95 (s, 1H), 7.47-7.43 (m, 1H), 7.38-7.30 (m, 2H), 4.69-4.60 (m, 1H), 4.23 (q, J=7.2 Hz, 2H), 3.87 (s, 2H), 1.42 (d, J=6.4 Hz, 6H), 1.29 (t, J=7.2 Hz, 3H). LCMS (ESI) m/z: 289.9 [M+1].

Compound 3H

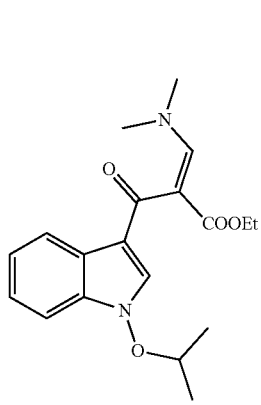

This compound was prepared according to the method of compound 1H in Embodiment 1, replacing compound 1G with compound 3G.

Compound 3I

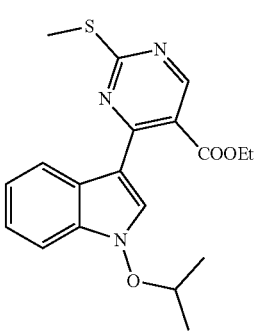

This compound was prepared according to the method of compound 1I in Embodiment 1, replacing compound 1H with compound 3H. $^1$H NMR (400 MHz, CDCl$_3$-d) δ=8.84 (s, 1H), 8.18 (d, J=8.0 Hz, 1H), 8.02 (s, 1H), 7.47 (d, J=8.0 Hz, 1H), 7.32 (dt, J=1.1, 7.6 Hz, 1H), 7.28-7.23 (m, 1H), 4.64 (spt, J=6.2 Hz, 1H), 4.30 (q, J=7.3 Hz, 2H), 2.70 (s, 3H), 1.43 (d, J=6.3 Hz, 6H), 1.22 (t, J=7.2 Hz, 3H). LCMS (ESI) m/z: 372.3 [M+1].

Compound 3J

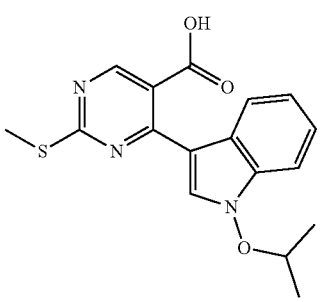

This compound was prepared according to the method of compound 2J in Embodiment 2, replacing compound 2I with compound 3I. $^1$H NMR (400 MHz, CDCl$_3$-d) δ=8.87 (s, 1H), 8.24 (d, J=7.8 Hz, 1H), 8.02 (s, 1H), 7.41 (d, J=8.1 Hz, 1H), 7.28-7.19 (m, 2H), 4.59-4.49 (m, 1H), 2.68 (s, 3H), 1.32 (d, J=5.9 Hz, 6H). LCMS (ESI) m/z: 344.2 [M+1].

Compound 3K

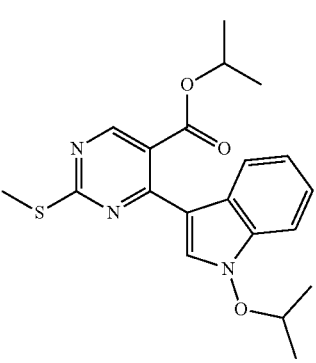

This compound was prepared according to the method of compound 2K in Embodiment 2, replacing compound 2J with compound 3J. $^1$H NMR (400 MHz, CDCl$_3$-d) δ=8.81 (s, 1H), 8.19-8.13 (m, 1H), 8.03 (s, 1H), 7.47 (d, J=8.1 Hz, 1H), 7.32 (dt, J=1.1, 7.6 Hz, 1H), 7.27-7.22 (m, 1H), 5.16

(spt, J=6.3 Hz, 1H), 4.63 (spt, J=6.2 Hz, 1H), 2.69 (s, 3H), 1.43 (d, J=6.1 Hz, 6H), 1.23 (d, J=6.1 Hz, 6H). LCMS (ESI) m/z: 386.3 [M+1].

Compound 3L

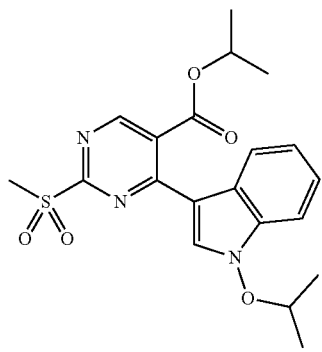

This compound was prepared according to the method of compound 1J in Embodiment 1, replacing compound 1I with compound 3K. ¹H NMR (400 MHz, CDCl₃-d) δ=9.00 (s, 1H), 8.41-8.36 (m, 1H), 8.17 (s, 1H), 7.52-7.48 (m, 1H), 7.41-7.31 (m, 2H), 5.38 (spt, J=6.2 Hz, 1H), 4.66 (spt, J=6.2 Hz, 1H), 3.43 (s, 3H), 1.43 (d, J=6.4 Hz, 6H), 1.32 (d, J=6.4 Hz, 6H). LCMS (ESI) m/z: 418.2 [M+1].

Compound 3M

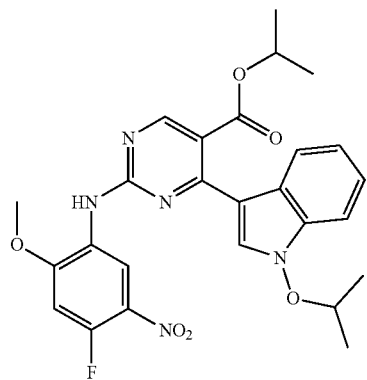

This compound was prepared according to the method of compound 1K in Embodiment 1, replacing compound 1J with compound 3L. ¹H NMR (400 MHz, CDCl₃-d) δ=9.53 (d, J=8.3 Hz, 1H), 8.83 (s, 1H), 8.04 (s, 1H), 7.79 (s, 1H), 7.76 (br d, J=8.1 Hz, 1H), 7.40 (d, J=8.1 Hz, 1H), 7.24-7.19 (m, 1H), 7.12 (dt, J=1.0, 7.6 Hz, 1H), 6.70 (d, J=12.2 Hz, 1H), 4.95-5.02 (m, 1H), 4.68-4.58 (m, 1H), 3.96 (s, 3H), 1.36 (d, J=6.1 Hz, 6H), 1.03 (d, J=6.1 Hz, 6H). LCMS (ESI) m/z: 524.2 [M+1].

Compound 3N

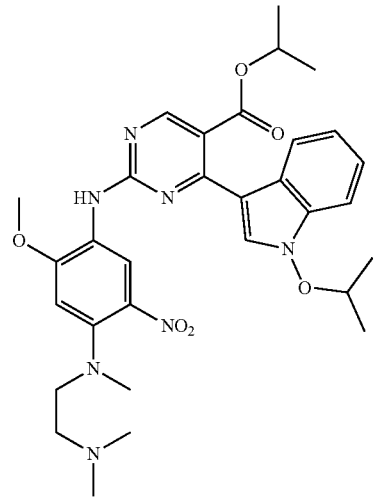

This compound was prepared according to the method of compound 1L in Embodiment 1, replacing compound 1K with compound 3M. ¹H NMR (400 MHz, CDCl₃-d) δ=9.19 (s, 1H), 8.80 (s, 1H), 8.02 (s, 1H), 7.80-7.72 (m, 1H), 7.68 (s, 1H), 7.38 (d, J=8.0 Hz, 1H), 7.18 (br d, J=1.0 Hz, 1H), 7.15-7.07 (m, 1H), 6.60 (s, 1H), 4.97 (quin, J=6.2 Hz, 1H), 4.62 (td, J=6.2, 12.4 Hz, 1H), 3.91 (s, 3H), 3.25-3.19 (m, 2H), 2.81 (s, 3H), 2.54-2.47 (m, 2H), 2.20 (s, 6H), 1.35 (d, J=6.0 Hz, 6H), 1.02 (d, J=6.3 Hz, 6H). LCMS (ESI) m/z: 606.2 [M+1].

Compound 3O

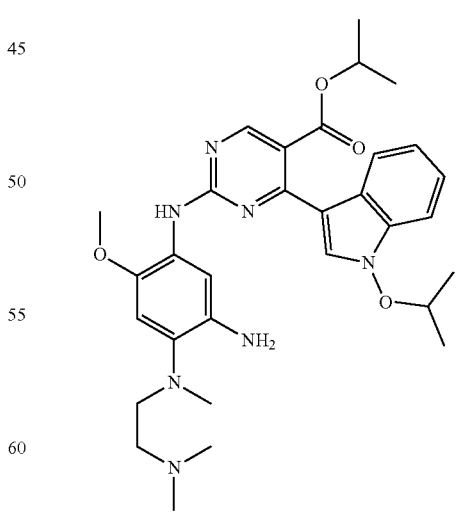

This compound was prepared according to the method of compound 1N in Embodiment 1, replacing compound 1M with compound 3N. LCMS (ESI) m/z: 576.3 [M+1].

Compound 3P

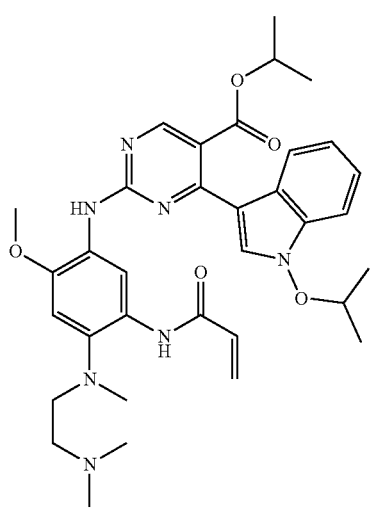

This compound was prepared according to the method of compound 1O in Embodiment 1, replacing compound 1N with compound 3O. LCMS (ESI) m/z: 630.2 [M+1].

Compound 3

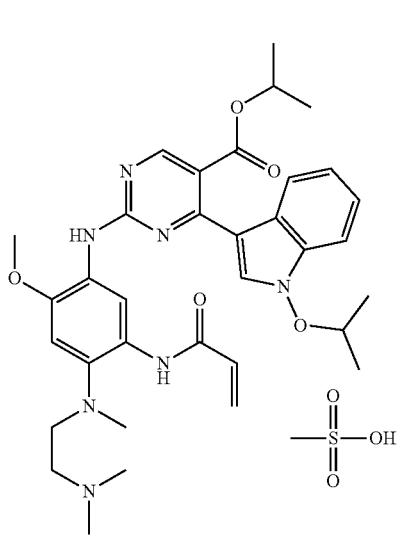

This compound was prepared according to the method of compound 1 in Embodiment 1, replacing compound 1O with compound 3P. ¹H NMR (400 MHz, Methanol-$d_4$) δ=8.69 (s, 1H), 8.47 (s, 1H), 7.97 (s, 1H), 7.79 (d, J=8.1 Hz, 1H), 7.38 (d, J=8.3 Hz, 1H), 7.17-7.10 (m, 1H), 7.04-6.98 (m, 1H), 6.86 (s, 1H), 6.37 (s, 1H), 6.35 (d, J=2.7 Hz, 1H), 5.79-5.73 (m, 1H), 4.95 (spt, J=6.2 Hz, 1H), 4.57 (spt, J=6.1 Hz, 1H), 3.90 (s, 3H), 3.38 (t, J=5.6 Hz, 2H)), 3.17 (t, J=5.6 Hz, 2H), 2.76 (s, 6H), 2.62-2.58 (m, 6H), 1.29 (d, J=6.1 Hz, 6H), 1.05 (d, J=6.1 Hz, 6H). LCMS (ESI) m/z: 630.2 [M+1].

Embodiment 4

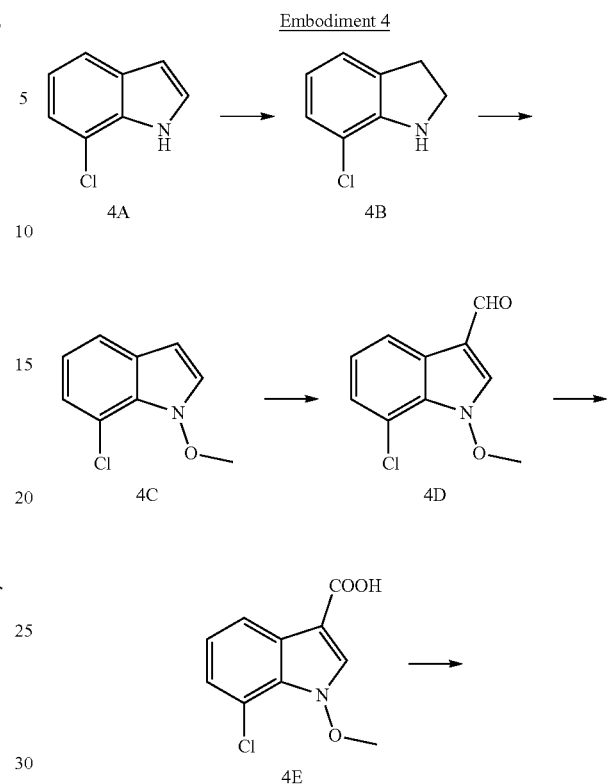

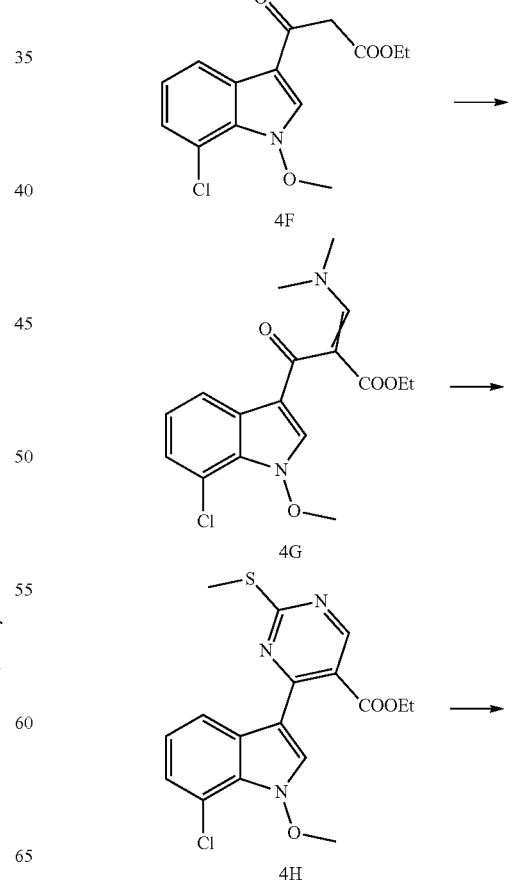

39
-continued
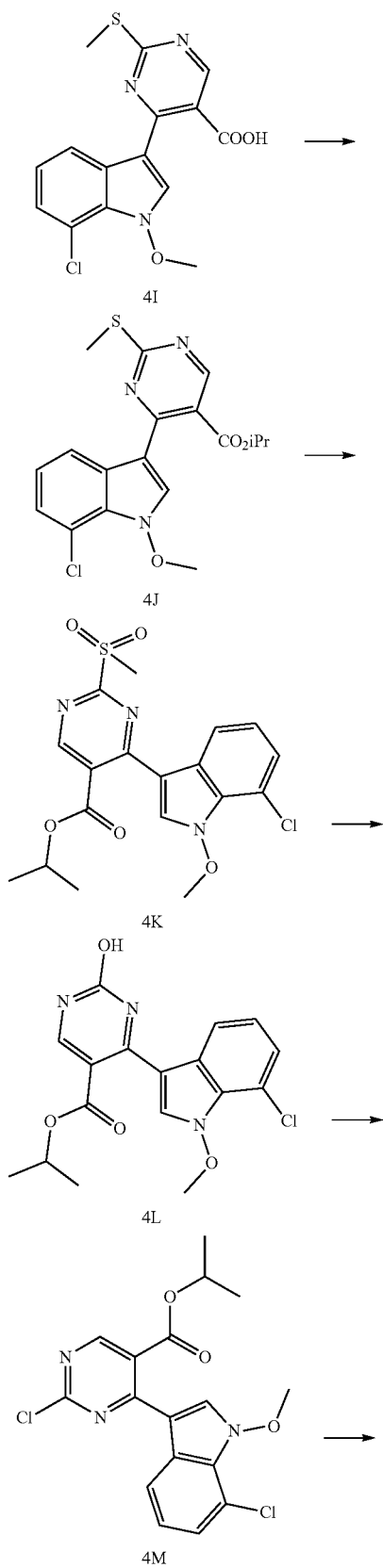
40
-continued
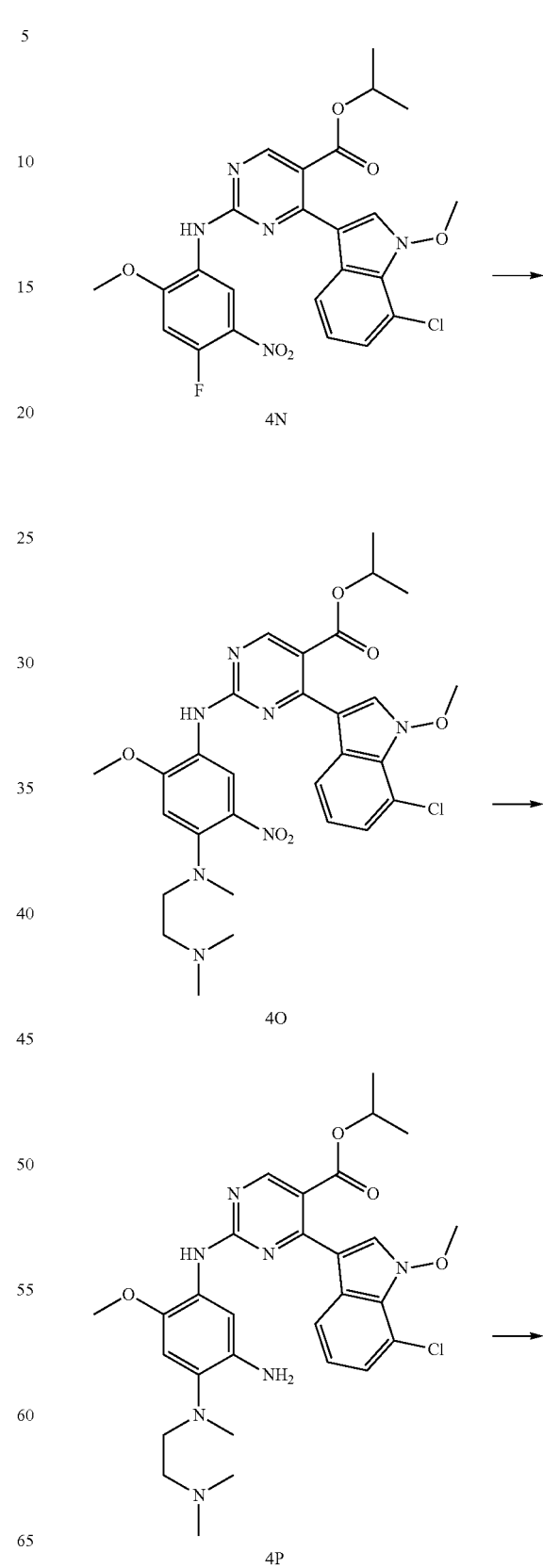

-continued

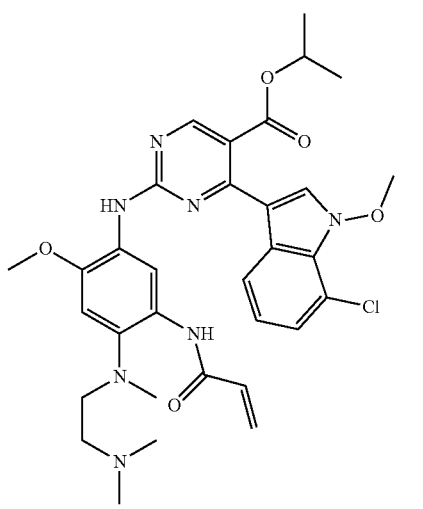

4Q

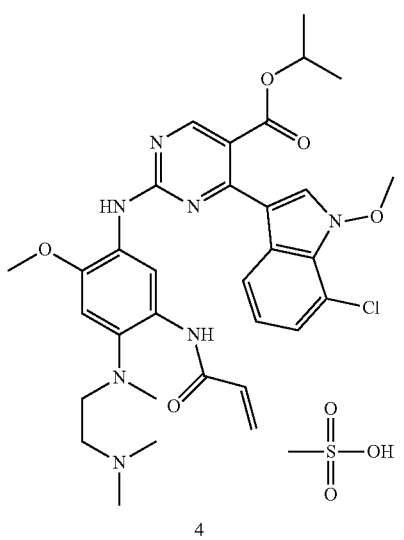

4

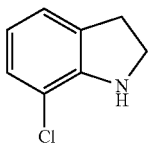

Compound 4B

Compound 4A (10.5 g, 69.26 mmol) was dissolved in acetic acid (50 mL), and sodium cyanoborohydride (13.06 g, 207.79 mmol) was added with an internal temperature controlled at 10° C. The reaction solution was stirred at 25° C. for 1 hour. The complete consumption of raw materials was monitored by TLC (PE/EA=1/0). Water (30.0 mL) was added to the reaction solution, and the pH of the reaction solution was adjusted to 7-8 with sodium hydroxide aqueous solution (2M), the mixture was extracted with ethyl acetate (80 mL×3 times), then the organic phases were combined, dried with anhydrous sodium sulfate and concentrated under reduced pressure. The crude product was purified by column chromatography (SiO$_2$, petroleum ether:ethyl acetate=1:0) to obtain the title compound. $^1$H NMR (400 MHz, CDCl$_3$-d) δ: 6.96-7.05 (m, 2H), 6.63 (t, J=7.64 Hz, 1H), 4.00 (br s, 1H), 3.63 (t, J=8.44 Hz, 2H), 3.12 (t, J=8.44 Hz, 2H).

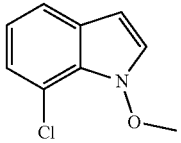

Compound 4C

Sodium tungstate (2.26 g, 6.86 mmol) was dissolved in water (30 mL), and the mixture was added dropwise to a solution of compound 4B (6.2 g, 40.36 mmol) in methanol (300 mL) at −20° C. Hydrogen peroxide (39.35 g, 347.12 mmol, 30% content) was dissolved in methanol (100 mL), and the mixture was added slowly dropwise to the reaction solution. After dropwise addition was completed, the reaction solution was stirred for 3 hours at 25° C. Potassium carbonate (44.63 g, 322.90 mmol) and dimethyl sulfate (8.15 g, 64.58 mmol) were added to the reaction solution, and the mixture was stirred for 15 min at 25° C. TLC (petroleum ether:ethyl acetate=20:1) showed that the raw material was completely consumed. The reaction solution was filtered and the filtrate was added with water (200.0 mL) and extracted with ethyl acetate (300 mL×3 times), and the combined organic phases were dried with anhydrous sodium sulfate and concentrated under reduced pressure. The residue was purified by column chromatography (SiO$_2$, petroleum ether: ethyl acetate=I/O) to obtain the title compound. $^1$H NMR (400 MHz, CDCl$_3$-d) δ 7.48 (dd, J=7.97, 0.82 Hz, 1H), 7.28 (d, J=3.39 Hz, 1H), 7.22 (dd, J=7.65, 0.63 Hz, 1H), 7.00-7.06 (m, 1H), 6.39 (d, J=3.51 Hz, 1H), 4.13 (s, 3H).

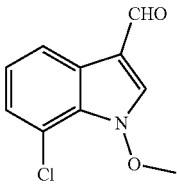

Compound 4D

This compound was prepared according to the method of compound 1E in Embodiment 1, replacing compound 1D with compound 4C. $^1$H NMR (400 MHz, CDCl$_3$-d) δ 9.98 (s, 1H), 8.22-8.28 (m, 1H), 7.91 (s, 1H), 7.33-7.37 (m, 1H), 7.21-7.27 (m, 1H), 4.22 (s, 3H).

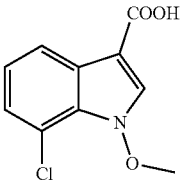

Compound 4E

This compound was prepared according to the method of compound 1F in Embodiment 1, replacing compound 1E for compound 4D. ¹H NMR (400 MHz, CDCl₃-d) δ 8.17 (dd, J=8.01, 0.79 Hz, 1H), 8.08 (s, 1H), 7.30-7.34 (m, 1H), 7.20-7.26 (m, 1H), 4.21 (s, 3H).

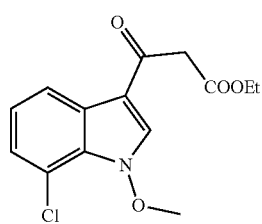

Compound 4F

This compound was prepared according to the method of compound 1G in Embodiment 1, replacing compound 1F with compound 4E. ¹H NMR (400 MHz, CDCl₃-d) δ 8.34 (dd, J=8.00, 1.00 Hz, 1H), 8.00 (s, 1H), 7.31-7.34 (m, 1H), 7.20-7.25 (m, 1H), 4.22-4.26 (m, 2H), 4.21 (s, 3H), 3.85 (s, 2H), 1.27-1.31 (m, 3H).

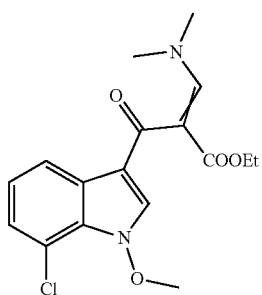

Compound 4G

This compound was prepared according to the method of compound 1H in Embodiment 1, replacing compound 1G with compound 4F.

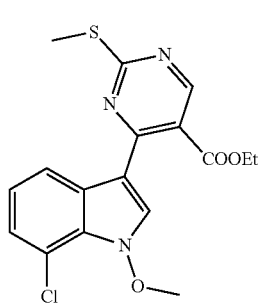

Compound 4H

This compound was prepared according to the method of compound 1I in Embodiment 1, replacing compound 1H with compound 4G. ¹H NMR (400 MHz, CDCl₃-d) δ 8.88 (s, 1H), 7.93-8.11 (m, 2H), 7.29 (dd, J=7.75, 0.75 Hz, 1H), 7.09-7.22 (m, 1H), 4.29 (q, J=7.13 Hz, 2H), 4.20 (s, 3H), 2.66 (s, 3H), 1.25-1.33 (m, 3H).

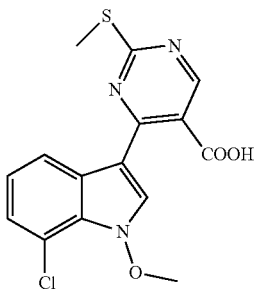

Compound 4I

This compound was prepared according to the method of compound 2J in Embodiment 2, replacing compound 2I with compound 4H. ¹H NMR (400 MHz, CDCl₃-d) δ 9.00 (s, 1H), 8.05-8.10 (m, 2H), 7.29 (dd, J=7.75, 0.75 Hz, 1H), 7.13-7.19 (m, 1H), 4.19 (s, 3H), 2.67 (s, 3H).

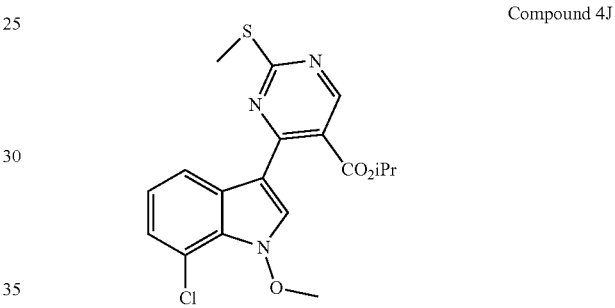

Compound 4J

This compound was prepared according to the method of compound 2K in Embodiment 2, replacing compound 2J with compound 4I. ¹H NMR (400 MHz, CDCl₃-d) δ 8.85 (s, 1H), 7.98-8.05 (m, 2H), 7.27-7.30 (m, 1H), 7.12-7.17 (m, 1H), 5.15 (m, 1H), 4.20 (s, 3H), 2.66 (s, 3H), 1.24 (s, 3H), 1.23 (s, 3H).

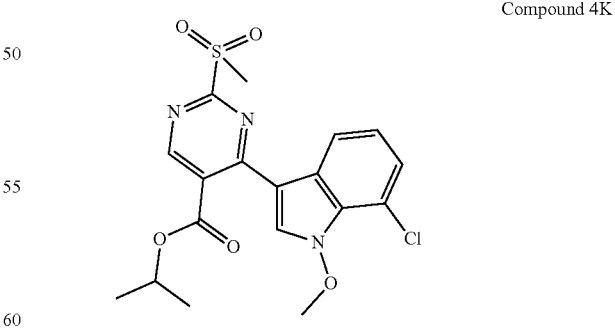

Compound 4K

This compound was prepared according to the method of compound 1J in Embodiment 1, replacing compound 1I with compound 4J. ¹H NMR (400 MHz, CDCl₃-d) δ 9.03 (s, 1H), 8.28 (d, J=8.07 Hz, 1H), 8.20 (s, 1H), 7.34 (d, J=7.58 Hz, 1H), 7.21-7.26 (m, 1H), 5.28 (m, 1H), 4.22 (s, 3H), 3.41 (s, 3H), 1.33 (s, 3H), 1.32 (s, 3H).

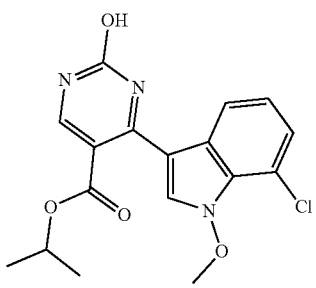

Compound 4L

This compound was prepared according to the method of compound 2M in Embodiment 2, replacing compound 2L with compound 4K. ¹H NMR (400 MHz, CDCl₃-d) δ 8.37-8.94 (m, 1H), 8.17 (s, 1H), 7.78-8.04 (m, 1H), 7.29 (br d, J=7.70 Hz, 1H), 7.15 (br t, J=7.89 Hz, 1H), 5.03-5.12 (m, 1H), 4.23 (s, 3H), 1.20 (br s, 3H), 1.18 (br s, 3H).

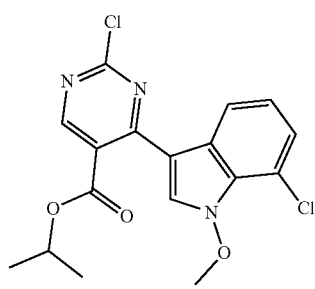

Compound 4M

This compound was prepared according to the method of compound 2N in Embodiment 2, replacing compound 2M with compound 4L. ¹H NMR (400 MHz, CDCl₃-d) δ 8.85 (s, 1H), 8.15 (s, 1H), 8.13 (dd, J=8.13, 1.00 Hz, 1H), 7.32 (dd, J=7.69, 0.81 Hz, 1H), 7.18-7.23 (m, 1H), 5.21 (m, 1H), 4.20 (s, 3H), 1.29 (s, 3H), 1.27 (s, 3H).

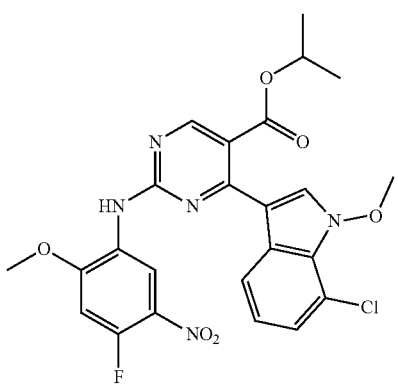

Compound 4N

This compound was prepared according to the method of compound 1K in Embodiment 1, replacing compound 1J with compound 4M. ¹H NMR (400 MHz, CDCl₃-d) δ 9.65 (d, J=8.25 Hz, 1H), 8.95 (s, 1H), 8.12 (s, 1H), 7.90 (s, 1H), 7.68 (br d, J=8.25 Hz, 1H), 7.29 (d, J=0.75 Hz, 1H), 7.11 (t, J=7.88 Hz, 1H), 6.79 (d, J=12.01 Hz, 1H), 5.07 (m, 1H), 4.27 (s, 3H), 4.05 (s, 3H), 1.15 (s, 3H), 1.14 (s, 3H)

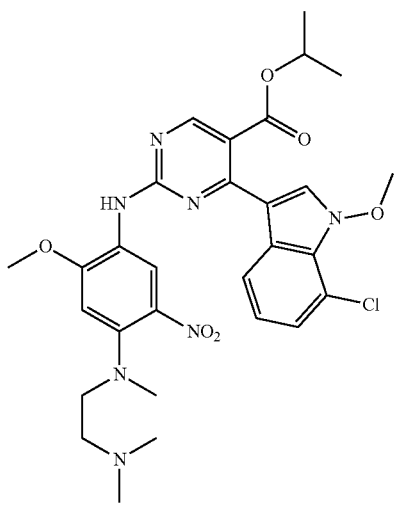

Compound 4O

This compound was prepared according to the method of compound 1L in Embodiment 1, replacing compound 1K with compound 4N. ¹H NMR (400 MHz, CDCl₃-d) δ 9.34 (s, 1H), 8.93 (s, 1H), 8.09 (s, 1H), 7.85 (s, 1H), 7.70 (br d, J=5.62 Hz, 1H), 7.24-7.26 (m, 1H), 7.08-7.14 (m, 1H), 6.80-6.87 (m, 1H), 5.07 (m, 1H), 4.26 (s, 3H), 4.05 (s, 3H), 3.50 (s, 4H), 2.91 (s, 3H), 2.44-2.68 (m, 6H), 1.15 (s, 3H), 1.14 (s, 3H).

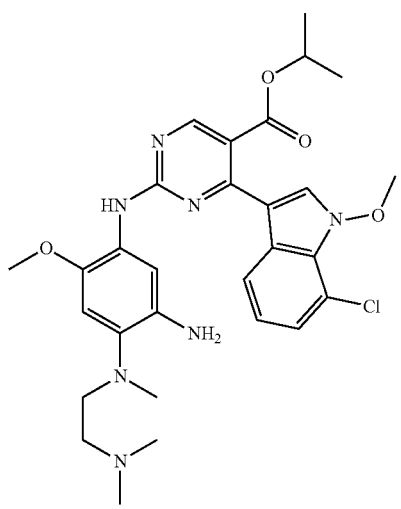

Compound 4P

This compound was prepared according to the method of compound 1N in Embodiment 1, replacing compound 1M with compound 4O.

Compound 4Q

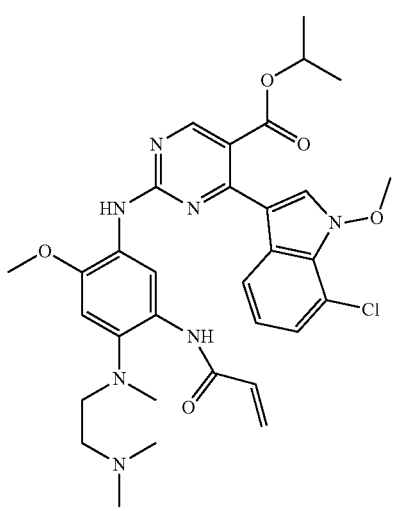

This compound was prepared according to the method of compound 1O in Embodiment 1, replacing compound 1N with compound 4P.

Compound 4

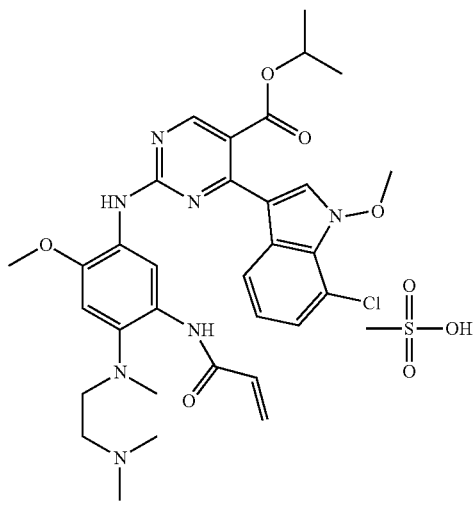

This compound was prepared according to the method of compound 1 in Embodiment 1, replacing compound 1O with compound 4Q. $^1$H NMR (400 MHz, Methanol-d$_4$) δ 9.06 (br s, 1H), 8.83 (d, J=0.88 Hz, 1H), 8.39 (br s, 1H), 7.65 (br d, J=6.88 Hz, 1H), 7.23 (br d, J=7.63 Hz, 1H), 7.06 (br t, J=7.82 Hz, 1H), 6.97 (br s, 1H), 6.50-6.58 (m, 1H), 6.40-6.47 (m, 1H), 5.83 (br d, J=9.76 Hz, 1H), 4.96-5.07 (m, 1H), 4.19 (s, 3H), 3.95 (s, 3H), 3.16 (br s, 2H), 2.65-2.70 (m, 5H), 2.44 (s, 6H), 1.43 (t, J=7.0 Hz, 3H), 1.12 (s, 3H), 1.10 (s, 3H).

Embodiment 5

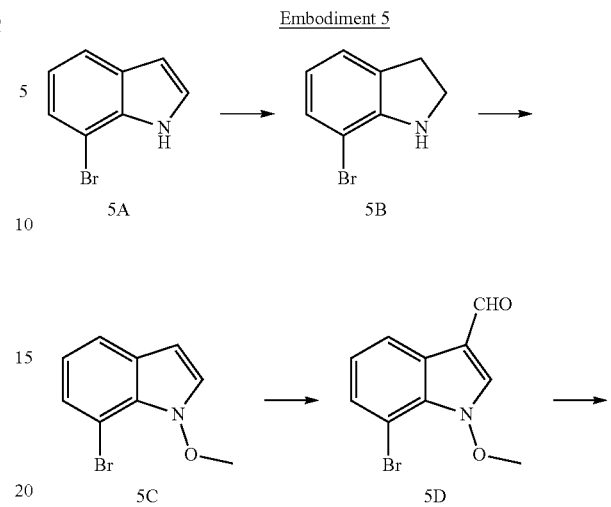

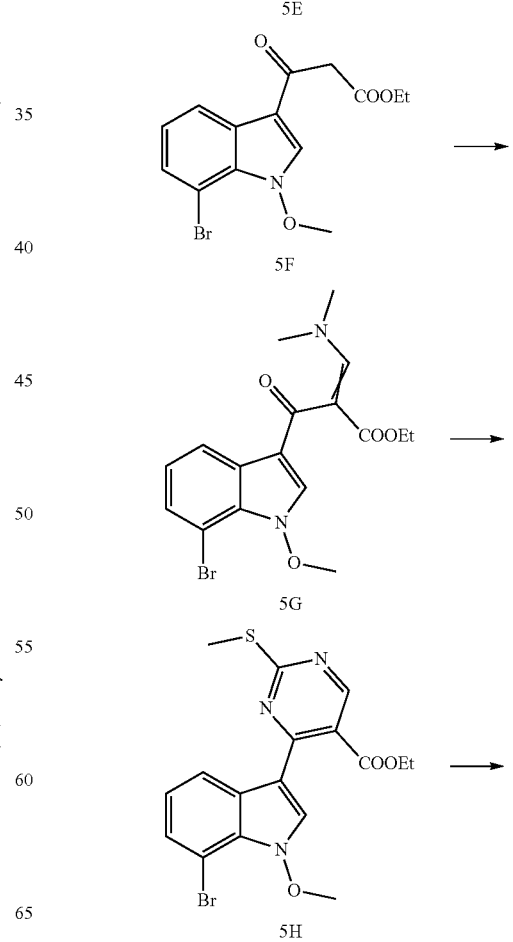

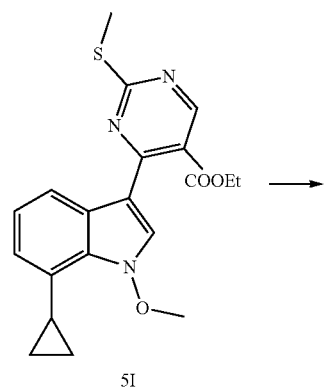
5I
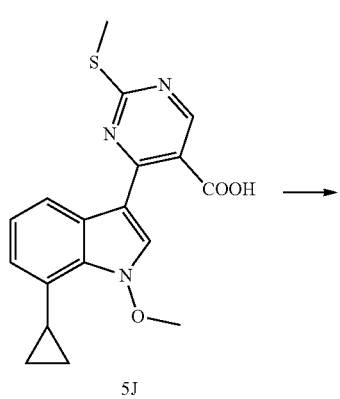
5J
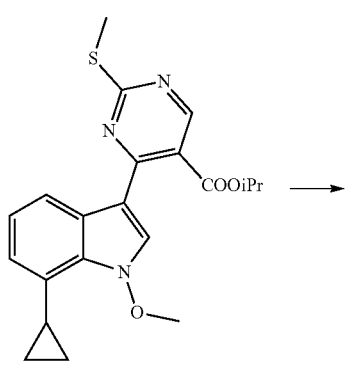
5K
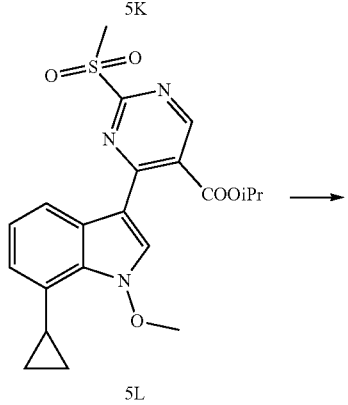
5L
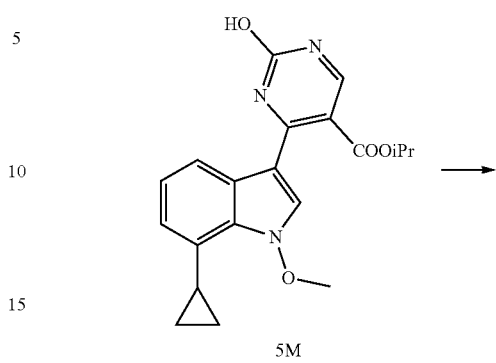
5M
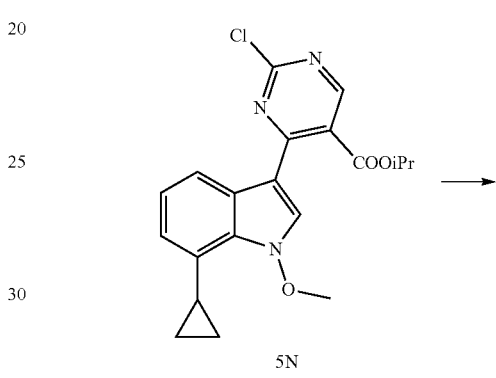
5N
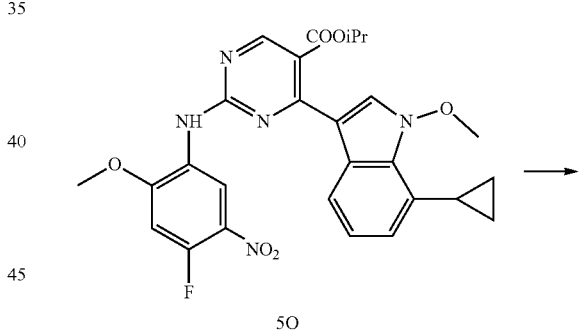
5O
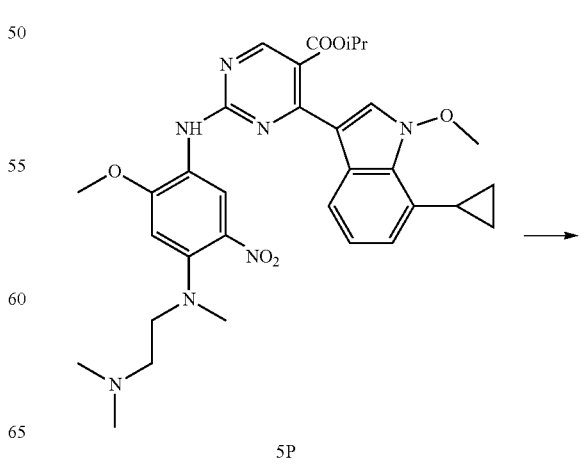
5P

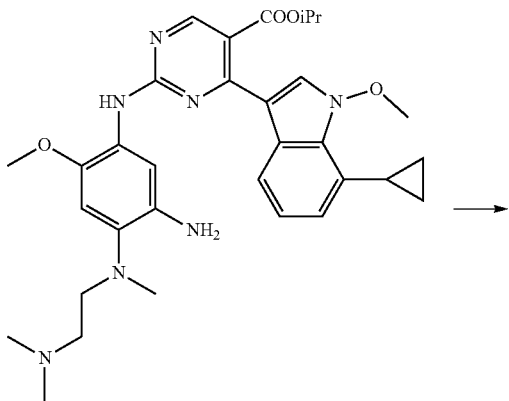

5Q

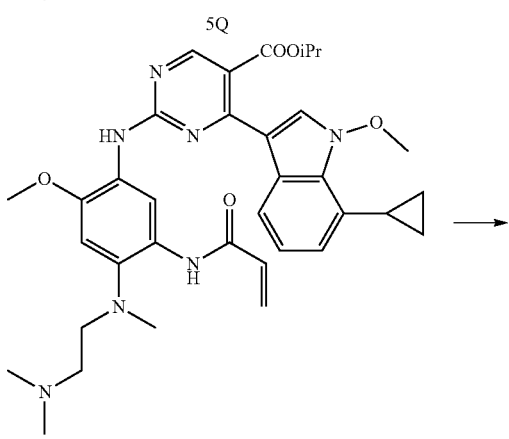

5R

Compound 5B

This compound was prepared according to the method of compound 4B in Embodiment 4, replacing compound 4A with compound 5A. ¹H NMR (400 MHz, CDCl₃-d) δ=7.17 (dd, J=0.6, 8.1 Hz, 1H), 7.04 (dd, J=1.1, 7.2 Hz, 1H), 6.62-6.52 (m, 1H), 4.08-3.71 (m, 1H), 3.62 (t, J=8.5 Hz, 2H), 3.16 (t, J=8.5 Hz, 2H).

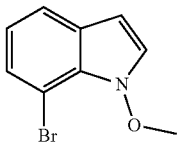

Compound 5C

This compound was prepared according to the method of compound 4C in Embodiment 4, replacing compound 4B with compound 5B. ¹H NMR (400 MHz, CDCl₃-d) δ=7.53 (dd, J=0.8, 7.9 Hz, 1H), 7.41 (d, J=7.6 Hz, 1H), 7.30 (d, J=3.5 Hz, 1H), 6.98 (t, J=7.8 Hz, 1H), 6.39 (d, J=3.5 Hz, 1H), 4.11 (s, 3H).

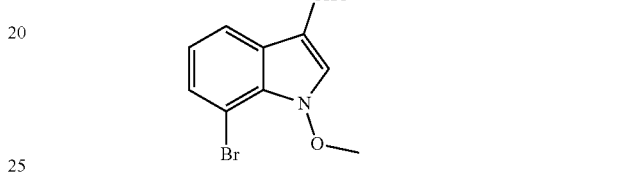

Compound 5D

This compound was prepared according to the method of compound 1E in Embodiment 1, replacing compound 1D with compound 5C. ¹H NMR (400 MHz, CDCl₃-d) δ=10.02-9.84 (m, 1H), 8.28 (dd, J=0.8, 7.9 Hz, 1H), 8.01 (s, 1H), 7.55-7.46 (m, 1H), 7.16 (t, J=7.8 Hz, 1H), 4.20 (s, 3H).

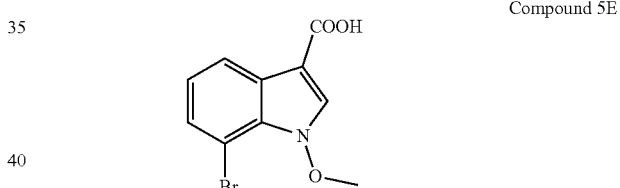

Compound 5E

This compound was prepared according to the method of compound 1F in Embodiment 1, replacing compound 1E with compound 5D. ¹H NMR (400 MHz, CDCl₃-d) δ=8.22 (d, J=7.9 Hz, 1H), 8.09 (s, 1H), 7.50 (d, J=7.5 Hz, 1H), 7.16 (t, J=7.9 Hz, 1H), 4.25 (s, 3H).

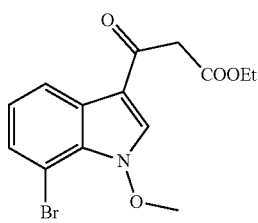

Compound 5F

This compound was prepared according to the method of compound 1G in Embodiment 1, replacing compound 1F with compound 5E. ¹H NMR (400 MHz, CDCl₃-d) δ=8.40 (d, J=0.9, 8.1 Hz, 1H), 8.02 (s, 1H), 7.51 (d, J=0.7, 7.6 Hz, 1H), 7.17 (t, J=7.9 Hz, 1H), 4.25-4.20 (m, 5H), 3.85 (s, 2H), 1.32-1.27 (m, 3H). LCMS (ESI) m/z: 342.1 [M+1].

Compound 5G

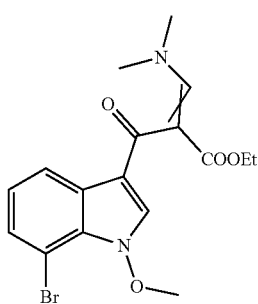

This compound was prepared according to the method of compound 1H in Embodiment 1, replacing compound 1G with compound 5F.

concentrated under reduced pressure, and water (10 mL) was added to the residue and the mixture was extracted with ethyl acetate (10 mL×2 times). The organic phases were combined, dried with anhydrous sodium sulfate and concentrated under reduced pressure, and the crude product was purified by column chromatography (SiO$_2$, petroleum ether: ethyl acetate=50:1 to 20:1) to obtain the title compound. $^1$H NMR (400 MHz, CDCl$_3$-d) δ=8.83 (s, 1H), 8.00 (s, 1H), 7.94 (d, J=8.0 Hz, 1H), 7.14 (t, J=7.7 Hz, 1H), 6.87 (d, J=7.4 Hz, 1H), 4.29 (q, J=7.2 Hz, 2H), 4.18 (s, 3H), 2.67 (s, 3H), 1.27 (s, 1H), 1.22 (t, J=7.1 Hz, 3H), 1.08-1.03 (m, 2H), 0.89-0.86 (m, 2H).

Compound 5H

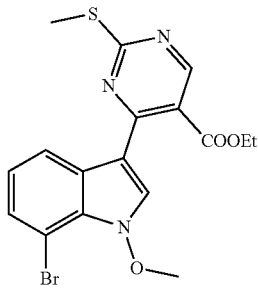

This compound was prepared according to the method of compound 1I in Embodiment 1, replacing compound 1H with compound 5G. $^1$H NMR (400 MHz, CDCl$_3$-d) δ=8.88 (s, 1H), 8.32-7.96 (m, 2H), 7.67-7.37 (m, 1H), 7.09 (t, J=7.9 Hz, 1H), 4.29 (q, J=7.1 Hz, 2H), 4.19 (s, 3H), 2.66 (s, 3H), 1.24 (t, J=7.1 Hz, 3H). LCMS (ESI) m/z: 421.9 [M+1].

Compound 5J

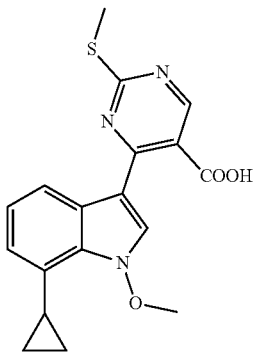

This compound was prepared according to the method of compound 2J in Embodiment 2, replacing compound 2I with compound 5I. $^1$H NMR (400 MHz, Methanol-d$_4$) δ=8.80 (s, 1H), 8.22-8.13 (m, 1H), 8.01 (dd, J=0.8, 8.1 Hz, 1H), 7.11 (t, J=7.8 Hz, 1H), 6.88 (d, J=7.4 Hz, 1H), 4.20 (s, 3H), 2.67 (s, 3H), 1.21-1.16 (m, 1H), 1.10-1.04 (m, 2H), 0.88-0.83 (m, 2H).

Compound 5I

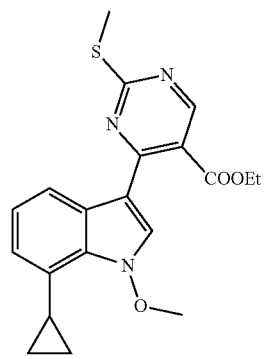

Compound 5H (1 g, 2.37 mmol) and cyclopropylboronic acid (407 mg, 4.74 mmol) were dissolved in toluene (5 mL) and water (5 mL); and cesium carbonate (926 mg, 2.84 mmol) and Pd(dppf)Cl$_2$·CH$_2$Cl$_2$ (200 mg, 244.91 μmol) were added and the mixture was stirred under nitrogen protection at 100° C. for 16 hours. The reaction solution was Compound 5K

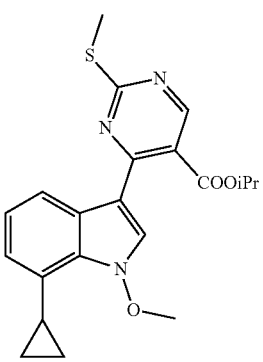

This compound was prepared according to the method of compound 2K in Embodiment 2, replacing compound 2J with compound 5J. $^1$H NMR (400 MHz, CDCl$_3$-d) δ=8.82-8.77 (m, 1H), 8.00 (s, 1H), 7.92 (dd, J=0.7, 8.1 Hz, 1H), 7.13 (t, J=7.8 Hz, 1H), 6.87 (d, J=7.4 Hz, 1H), 5.14 (m, 1H), 4.17 (s, 3H), 2.67 (s, 3H), 1.28-1.25 (m, 1H), 1.22 (d, J=6.3 Hz, 6H), 1.07-1.01 (m, 2H), 0.90-0.84 (m, 2H).

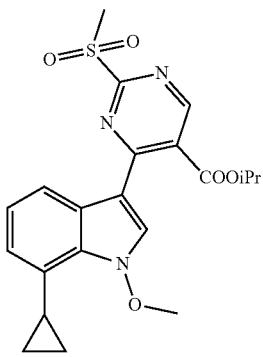

Compound 5L

This compound was prepared according to the method of compound 1J in Embodiment 1, replacing compound 1I with compound 5K. $^1$H NMR (400 MHz, CDCl$_3$-d) δ=8.99 (s, 1H), 8.15 (s, 1H), 8.12 (d, J=7.6 Hz, 1H), 7.22 (t, J=7.8 Hz, 1H), 6.92 (d, J=7.5 Hz, 1H), 5.26 (m, 1H), 4.20 (s, 3H), 3.41 (s, 3H), 2.67 (tt, J=5.3, 8.4 Hz, 1H), 1.33-1.28 (m, 6H), 1.10-1.05 (m, 2H), 0.91-0.86 (m, 2H).

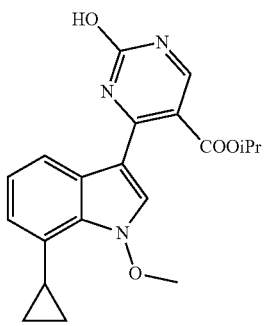

Compound 5M

This compound was prepared according to the method of compound 2M in Embodiment 2, replacing compound 2L with compound 5L. $^1$H NMR (400 MHz, CDCl$_3$-d) δ=9.01-8.60 (m, 1H), 8.14 (br s, 1H), 7.81-7.33 (m, 1H), 7.09 (br t, J=7.4 Hz, 1H), 6.85 (br d, J=7.3 Hz, 1H), 5.09-4.95 (m, 1H), 4.29 (s, 3H), 2.71-2.60 (m, 1H), 1.12 (br d, J=5.6 Hz, 6H), 1.04 (br d, J=8.2 Hz, 2H), 0.85 (br d, J=4.8 Hz, 2H).

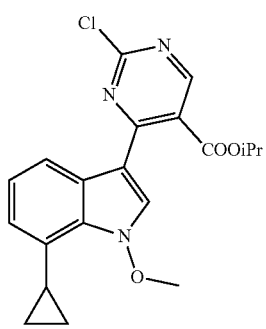

Compound 5N

This compound was prepared according to the method of compound 2N in Embodiment 2, replacing compound 2M with compound 5M. $^1$H NMR (400 MHz, CDCl$_3$-d) δ=8.84-8.76 (m, 1H), 8.17-8.09 (m, 1H), 8.00 (dd, J=0.7, 8.1 Hz, 1H), 7.18 (t, J=7.8 Hz, 1H), 6.90 (d, J=7.4 Hz, 1H), 5.19 (spt, J=6.3 Hz, 1H), 4.19 (s, 3H), 2.67 (tt, J=5.3, 8.4 Hz, 1H), 1.26 (d, J=6.4 Hz, 6H), 1.08-1.03 (m, 2H), 0.90-0.85 (m, 2H).

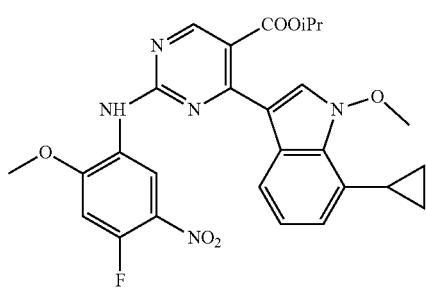

Compound 5O

This compound was prepared according to the method of compound 1K in Embodiment 1, replacing compound 1J with compound 5N. $^1$H NMR (400 MHz, CDCl$_3$-d) δ=9.71 (d, J=8.3 Hz, 1H), 8.91 (s, 1H), 8.13 (s, 1H), 7.87 (s, 1H), 7.61-7.50 (m, 1H), 6.85 (d, J=7.3 Hz, 1H), 6.78 (d, J=12.0 Hz, 1H), 5.05 (td, J=6.3, 12.5 Hz, 1H), 4.26 (s, 3H), 4.04 (s, 3H), 2.75-2.65 (m, 1H), 1.11 (d, J=6.1 Hz, 6H), 1.07-1.04 (m, 2H), 0.89-0.85 (m, 2H).

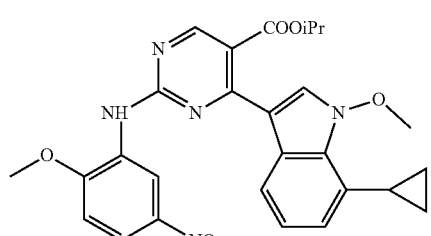

Compound 5P

This compound was prepared according to the method of compound 1L in Embodiment 1, replacing compound 1K with compound 5O. $^1$H NMR (400 MHz, CDCl$_3$-d) δ=9.38 (br s, 1H), 8.88 (s, 1H), 8.12 (s, 1H), 7.78 (s, 1H), 7.54 (br d, J=5.9 Hz, 1H), 7.08 (t, J=7.7 Hz, 1H), 6.84 (d, J=7.4 Hz, 1H), 6.67 (s, 1H), 5.03 (td, J=6.3, 12.5 Hz, 1H), 4.25 (s, 3H), 3.98 (s, 3H), 3.32-3.27 (m, 2H), 2.90 (s, 3H), 2.74-2.67 (m, 1H), 2.58 (t, J=7.1 Hz, 2H), 2.27 (s, 6H), 1.10 (br d, J=6.3 Hz, 6H), 1.06-1.01 (m, 2H), 0.87-0.83 (m, 2H).

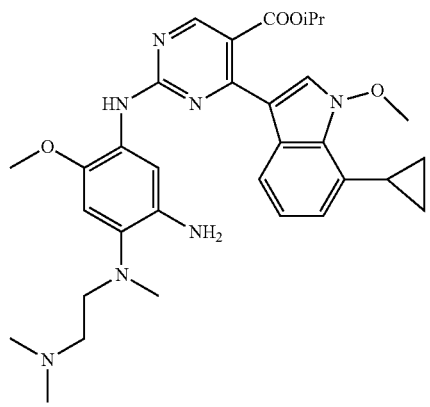

Compound 5Q

This compound was prepared according to the method of compound 1N in Embodiment 1, replacing compound 1M with compound 5P. $^1$H NMR (400 MHz, CDCl$_3$-d) δ=8.88 (s, 2H), 8.17 (br d, J=13.3 Hz, 1H), 7.98 (br s, 3H), 7.17 (br s, 1H), 7.05-6.96 (m, 1H), 6.89 (br d, J=16.5 Hz, 1H), 6.73 (br s, 1H), 5.11 (br d, J=6.3 Hz, 1H), 4.19 (br s, 3H), 3.85 (br s, 3H), 2.78 (br s, 2H), 2.56 (br s, 6H), 2.42 (br s, 2H), 2.27 (br s, 3H), 1.24 (br s, 6H), 1.07-1.03 (m, 2H), 0.83-0.76 (m, 2H).

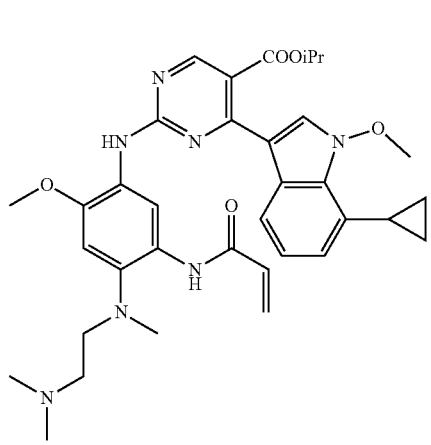

Compound 5R

This compound was prepared according to the method of compound 1O in Embodiment 1, replacing compound 1N with compound 5Q.

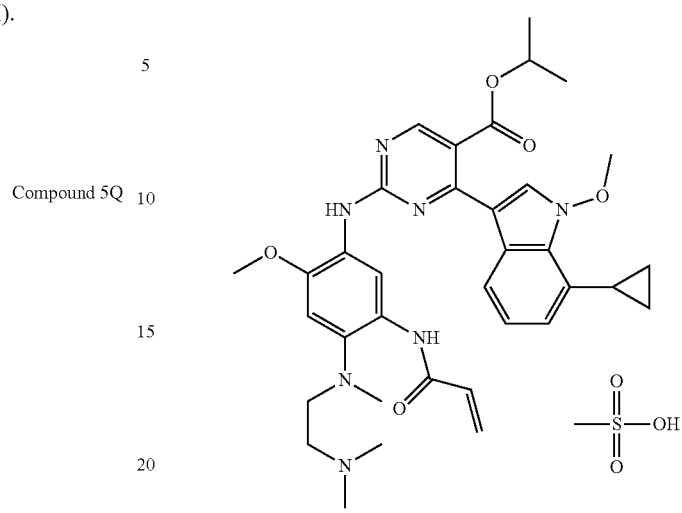

Compound 5

This compound was prepared according to the method of compound 1 in Embodiment 1, replacing compound 1O with compound 5R. $^1$H NMR (400 MHz, Methanol-d$_4$) δ=8.77 (s, 1H), 8.46 (br s, 1H), 8.13 (s, 1H), 7.71 (d, J=7.9 Hz, 1H), 7.01 (t, J=7.8 Hz, 1H), 6.96 (s, 1H), 6.82 (d, J=7.6 Hz, 1H), 6.48-6.42 (m, 2H), 5.91-5.77 (m, 1H), 5.07 (td, J=6.2, 12.5 Hz, 1H), 4.18 (s, 3H), 3.99 (s, 3H), 3.52-3.46 (m, 2H), 3.27-3.24 (m, 2H), 2.86 (s, 6H), 2.70 (d, J=4.8 Hz, 6H), 1.28 (s, 1H), 1.17 (d, J=6.2 Hz, 6H), 1.10-1.04 (m, 2H), 0.85-0.80 (m, 2H).

Experimental Embodiment 1 Compound Stability Test in Plasma of Different Species In this study, mouse, SD rat, Beagle, cynomolgus monkey and human plasma were used as materials to investigate the stability of the tested compounds in the plasma of the above five species. Propantheline, Enalapril, Bisacodyl and Procaine were used as control compounds.

The experimental conditions for the test compounds were as follows:
test concentration: 2 μM (DMSO ≤0.5%);
incubation times: 0, 10, 30, 60 and 120 minutes;
frozen plasma (from multiple species) was used in the test system;
incubation conditions: 37° C.

The mixed frozen plasma was thawed in a 37° C. water bath prior to the experiment. Plasma was centrifuged at 4000 rpm for 5 minutes and cleared if there was a clot. The pH will be adjusted to 7.4±0.1 if required.

The intermediate solution of 1 mM compound and positive control was prepared by diluting 10 mM stock solution with 90 μL of dimethyl sulfoxide. 100 μM solution was prepared by diluting 20 μL of intermediate solution (1 mM) with 180 μL of 45% methanol/water.

2 μL of 100 μM solution was added to 98 μL of blank plasma to achieve a final concentration of 2 μM (in duplicate) of the sample, and the sample was incubated in a 37° C. water bath. At each time point (0, 10, 30, 60 and 120 min), 400 μL of termination solution (200 ng/mL toluenesulfonylurea and 200 ng/mL labetalol, 50% ACN/MeOH) was added to precipitate the proteins and mixed thoroughly.

The sample plate was centrifuged at 4000 rpm for 10 minutes. A small portion of the supernatant (50 μL) was transferred from each well and mixed with 100 μL of ultrapure water. Samples were vibrated at 800 rpm for approximately 10 minutes prior to LC-MS/MS analysis.

The formula used for data processing was as follows:

% residual amount=(peak area ratio of control to internal standard at any time point/peak area ratio of control to internal standard at 0 min)×10000. Experimental results: see Tables 1 and 2.

TABLE 1

In vitro plasma stability of compounds

| In vitro plasma stability (Residual percentage at different time points) | Compound 1 |
| --- | --- |
| Human 120 minutes | 19% |
| Monkey 120 minutes | 93.7% |
| Dog 120 minutes | 101.7% |
| Rat 120 minutes | 87.9% |
| Mouse 120 minutes | 45% |

TABLE 2

In vitro plasma half-life of compounds

| Half-life of different species $T_{1/2}$ (min) | Compound 1 |
| --- | --- |
| Human $T_{1/2}$ | 51.6 |
| Monkey $T_{1/2}$ | >289.1 |
| Dog $T_{1/2}$ | >289.1 |
| Rat $T_{1/2}$ | >289.1 |
| Mouse $T_{1/2}$ | 108.8 |

Experimental Conclusions:

As can be seen from Tables 1 and 2, the compounds of the present disclosure have better plasma stability in different species.

Experimental Embodiment 2 Biochemical Experiment

Experimental Purposes:

To detect the inhibitory effect of compounds on EGFR WT, EGFR (D770_N771insNPG), ERBB2 (V777_G778ins>CG), EGFR T790M/L858R enzyme activities Experimental Material:

EGFR WT (Invitrogen, Cat. No. PR7295B), EGFR [L858R] (Invitrogen, Cat. No. PR7447A), EGFR [d746-750] (Invitrogen, Cat. No. PV6179), ATP (Sigma, Cat. No. A7699-1G), DMSO (Sigma, Cat. No. D2650), DTT (Sigma, Cat. No. 43815), 384-well plate, compound dilution plate (Greiner, Cat. No. 781280), 384-well plate, test plate (Perkin Elmer, Cat. No. 6007299), HTRF KinEASE TK Kit (Cisbio, Cat. No. 62TK0PEB), magnesium chloride (Sigma, Cat. No. M1028), Orthovanadate (Sigma, Cat. No. 56508), BSA (Sigma, Cat. No. A7030), HEPES (Life technology, Cat. No. 11344-041).

Experimental Methods:

Final test concentrations of compounds:

The final test concentrations of the test compounds ranged from 10 μM to 0.17 nM in 3-fold gradient dilutions at 11 concentrations.

Kinase Assay:

The preparation of the buffer, 50 mM HEPES (pH 7.5), 0.01% BSA, 5 mM $MgCl_2$, and 0.1 mM Orthovanadate were contained in the buffer. After the preparation of the buffer, the enzyme and substrate were mixed with pre-diluted prepared compounds of different concentrations, and the mixture was placed at room temperature for 15 minutes. The reaction was initiated by adding ATP and incubated for 60 min at room temperature (wherein negative and positive control were set). 2.5 μL of compound, 5 μL of enzyme and substrate mixture and 2.5 μL of ATP were contained in the 10 μL reaction system. After the reaction was completed, the antibody was added to the assay, incubated at room temperature for 60 minutes and then detected by Envision (plate reading instrument), and data were collected. Data analysis and plotting were performed according to XLfit5 software (data analysis software).

Experimental results: see Table 3.

TABLE 3

Inhibitory activity of compounds on enzymes

| Enzyme $IC_{50}$(nM) | | Compound 1 |
| --- | --- | --- |
| Wild-type EGFR enzymes | / | 0.39 |
| EGFR exon 20 insertion (D770_N771insNPG) enzyme | 0.8 | 0.7 |
| EGFR L858R/T790M double mutant enzyme | 3.71 | / |
| HER2 exon 20 insertion (V777_G778ins > CG) enzyme | 1.86 | / |

Note:
"/" means not tested.

Experimental Conclusions:

The compounds of the present disclosure have better enzyme activity against both EGFR exon 20 insertion mutation and ERBB2 exon 20 insertion mutation, as well as against L858R and T790M double mutations.

Experimental Embodiment 3 Anti-Proliferation Experiment of Compounds on Cells (1) Anti-Proliferation Activity Test of LU-0387 (EGFR Exon 20 NPH Insertion Mutation) Cells Experimental Materials:

Fetal bovine serum FBS, CellTiter Glo® luminescent cell activity assay, 96-well clear flat-bottomed black-walled plate Experimental Instruments:

EnVision Multilabel Microplate Detector, PerkinElmer Instrument Co., Ltd, model: 2104-0010A;

$CO_2$ incubator, Thermo Fisher Scientific, model: 3100 Series;

Biological Safety Cabinet, Thermo Fisher Scientific, model: 1300 Series A2;

Inverted microscope, Olympus, model: CKX41SF;

Electronic balance, METTLER TOLEDO, model: AL-104;

Refrigerator, Siemens, model: KK25E76TI.

Experimental Steps:

A cell counter was used for cell counting, and cell viability was detected to ensure that the viability of each cell line was above 90%. Cell suspension was added to a 96-well plate to bring the cell density to the specified concentration and incubated overnight at 37° C., 5% $CO_2$ and 95% humidity. The culture medium was added to the T0 plate, the CTG reagent was melted and the cell plate was equilibrated at room temperature. CTG solution was added to each well. The cell plate was vibrated to lyse the cells and the cold light values were read. The compound to be test and the control drug were diluted in a gradient to obtain a 10-fold solution. 10 μL of drug solution was added to each well of a 96-well plate that had been inoculated with cells. The incubation was continued at 37° C., 5% $CO_2$, 95% humidity for 4 days, and CTG analysis was performed and cold light values were read separately. The data were analyzed using GraphPad Prism 5.0 software and $IC_{50}$ values were calculated.

Experimental Results:

The $IC_{50}$ data of the compounds of the present disclosure against EGFR exon 20 insertion mutation NPH in LU-0387 cells are shown in Table 4.

Experimental Conclusions:

The compounds of the present disclosure exhibit better inhibitory activity against EGFR exon 20 insertion mutations.

(2) Anti-Proliferation Activity Test of the Compound Against H1975 Cells and $IC_{50}$ Test of Anti-Proliferation Activity Against A431 Cells Experimental Materials:

RPMI1640 medium, FBS fetal bovine serum, trypsin-EDTA, were all purchased from Giboco. DPBS was purchased from Corning, penicillin/streptomycin solution was purchased from Hyclone, and Cell-Titer Glo reagent was purchased from Promega (1kit, Cat. No. G7571). Plate reading instrument: Envision (PerkinElmer).

Experimental Methods:

384-well plates in columns 1, 2, and 24 were added with 45 μL of medium, and the cell suspension was dispensed with Multi-drop at 45 μL per well (1000 cells) and incubated overnight in an incubator. The compound was added to the source plate according to the Echo dispensing requirements, the compound in the source plate was added to the inter plate and diluted to an intermediate concentration, then the compound in the source plate and the inter plate was added to the cell plate, and the cells were continued to be incubated in a incubator for 72 hours. After 72 hours, Cell-Titer Glo reagent and cells were removed and equilibrated at room temperature for 30 min. 25 μL of Cell-Titer Glo reagent was dispensed into 384-well plates with Multi-drop, the cell plate was vibrated at medium speed for 3 min, centrifuged at 1000 rpm for 2 min, and stood for 10 min. The plate was read by Envision (Luminescence).

The data of the anti-proliferation activity $IC_{50}$ against H1975 cells and the anti-proliferation activity $IC_{50}$ against A431 cells of the compounds of the present disclosure are shown in Table 4.

TABLE 4

Anti-proliferation activity data of compounds against cells

| Cell $IC_{50}$(nM) | LU0387 EGFR-H773_V774insNPH | H1975 (L858R/T790M) | A431 |
|---|---|---|---|
| Compound 1 | 25.6 | 15.3 | 335 |

Experimental Results:

The compounds of the present disclosure have very good anti-proliferation activity against H1975 (L858R/T790M) cells, LU0387 EGFR-H773_V774insNPH (exon 20 insertion mutation), and weak inhibitory effect against A431 (EGFR wild type), indicating that the compounds of the present disclosure has better selectivity.

Experimental Embodiment 4 Anti-Proliferation Experiment of Compound Against Ba/F3 Exon 20 Insertion Mutant Cells Experimental Material:

RPMI1640 medium was purchased from Hyclone, FBS fetal bovine serum was purchased from GBICO, and trypsin-EDTA were both purchased from Giboco. DPBS was purchased from Corning, penicillin/streptomycin solution was purchased from Hyclone, and Cell-Titer Glo reagent was purchased from Promega (Cat. No. G7572). Ba/F3 EGFR-D770_N771insSVD, Ba/F3 EGFR-H773_V774insNPH, Ba/F3 EGFR-V769_D770insASV, BaF3 ERBB2 A775_G776 ins YVMA, the cell lines were constructed by Beijing Kang Yuan Bochuang Biotechnology Co., Ltd. Plate reading instrument: Envision (PerkinElmer).

Experimental Methods:

Cells in logarithmic growth phase were harvested and cell counts were performed using a platelet counter. Cell viability was detected by the Taipan Blue rejection assay. The cell concentration was adjusted; the cell suspension was added to a 96-well plate separately. Cells in 96-well plates were incubated overnight at 37° C., 5% $CO_2$, and 95% humidity. To prepare the drug solution, 10 μL of drug solution was added to each well of the 96-well plate inoculated with cells, and three replicate wells were set up for each drug concentration. The cells in the 96-well plates added with drugs were placed at 37° C., 5% $CO_2$, 95% humidity and continued to incubate for 72 hours, after which CTG analysis was performed and the cells were vibrated on an orbital shaker to lyse the cells. The cell plate was placed at room temperature to stabilize the cold light signal, and the cold light values were read. The data were analyzed using GraphPad Prism 7.0 software, and a nonlinear S-curve regression was used to fit the data to derive the dose-effect curve from which the $IC_{50}$ values were calculated.

The $IC_{50}$ of anti-proliferation activity against Ba/F3 Exon20 insertion mutant cells of the compounds of the present disclosure is shown in Table 5.

TABLE 5

Anti-proliferation activity data of compounds against Ba/F3 exon 20 insertion mutant cells

| Mutant cells $IC_{50}$ (nM) | Compound 1 | Compound 2 | Compound 3 | Compound 4 | Compound 5 |
|---|---|---|---|---|---|
| Ba/F3 EGFR-D770_N771insSVD | 27 | 24 | 27 | 54 | 33 | 58 |
| Ba/F3 EGFR-H773_V774insNPH | / | 15 | / | / | / | / |
| Ba/F3 EGFR-V769_D770insASV | / | 7 | / | / | / | / |
| BaF3 ERBB2 A775_G776 ins YVMA | / | 37 | / | / | / | / |

Note:
"/" means not tested.

Experimental Conclusions:

Ba/F3 exon 20 insertion mutant cells are cell lines with SVD, NPH, ASV, and YVMA insertion mutations artificially constructed using mouse B cells, and it can be seen from Table 5 that the compounds of the present disclosure have better cellular anti-proliferation activity against the more frequent exon 20 insertion mutations such as SVD, NPH, ASV, and YVMA, and also show better anti-proliferation activity against common exon 20 insertion mutations such as SVD mutation.

Embodiment 5 In Vivo Pharmacodynamic Study of Mouse Lung Cancer NCI-H1975 Cells Subcutaneous Xenograft Tumor BALB/c Nude Mouse Model Cell Culture:

Human lung cancer NCI-H1975 cells were cultured in vitro in a monolayer under the conditions of 1640 medium with 10% fetal bovine serum, 1% double antibodies and incubated at 37° C. in a 5% $CO_2$ incubator. Routine treatment passages were performed twice a week. When the cell saturation was 80%-90% and the number reached the required level, the cells were collected, counted, and inoculated.

Animals:

BALB/c nude mice, female, 6-8 weeks old, weighing 18-22 g. Provided by Shanghai Xipuer-Bikai Laboratory Animal Co., Ltd. or other qualified suppliers.

Tumor Inoculation:

Tumor tissue was collected from H1975 tumor-bearing mice of human lung cancer xenograft model, cut into 2-3 mm diameter tumor blocks and inoculated subcutaneously at the right anterior scapula of Balb/c nude mice. When the average tumor volume was 145 $mm^3$, the tumors were randomly grouped according to their size, and the day of grouping was defined as day 0.

Tumor Measurements and Experimental Indexes:

The experimental index was to examine whether tumor growth was inhibited, delayed or cured. Tumor diameters were measured with vernier calipers twice a week. The calculation formula of tumor volume was: $V=0.5a \times b^2$, wherein a and b represented the long and short diameters of the tumor, respectively. The antitumor efficacy of the compounds was evaluated by TGI (%) or relative tumor proliferation rate T/C (%). TGI (%), reflecting the tumor growth inhibition rate. Calculation of TGI (%): TGI (%)=[(1-(average tumor volume at the end of administration of a treatment group−average tumor volume at the beginning of administration of this treatment group))/(average tumor volume at the end of treatment in the solvent control group−average tumor volume at the beginning of treatment of the solvent control group)]×100%. Relative tumor proliferation rate T/C (%): The calculation formula was as follows: T/C %=$T_{RTV}/C_{RTV}$×100% ($T_{RTV}$: RTV in the treatment group; $C_{RTV}$: RTV in the negative control group). The relative tumor volume (RTV) was calculated according to the results of tumor measurement, and the formula was RTV=$V_t/V_0$, wherein $V_0$ was the average tumor volume measured at the time of group administration (i.e., $d_0$), and $V_t$ was the average tumor volume at a certain measurement, $T_{RTV}$ and $C_{RTV}$ were taken on the same day. After the experiment, the tumor weight will be detected, and the percentage of $T/C_{weight}$ will be calculated. $T_{weight}$ and $C_{weight}$ represented the tumor weight of the administration group and the solvent control group, respectively.

Figure 2:
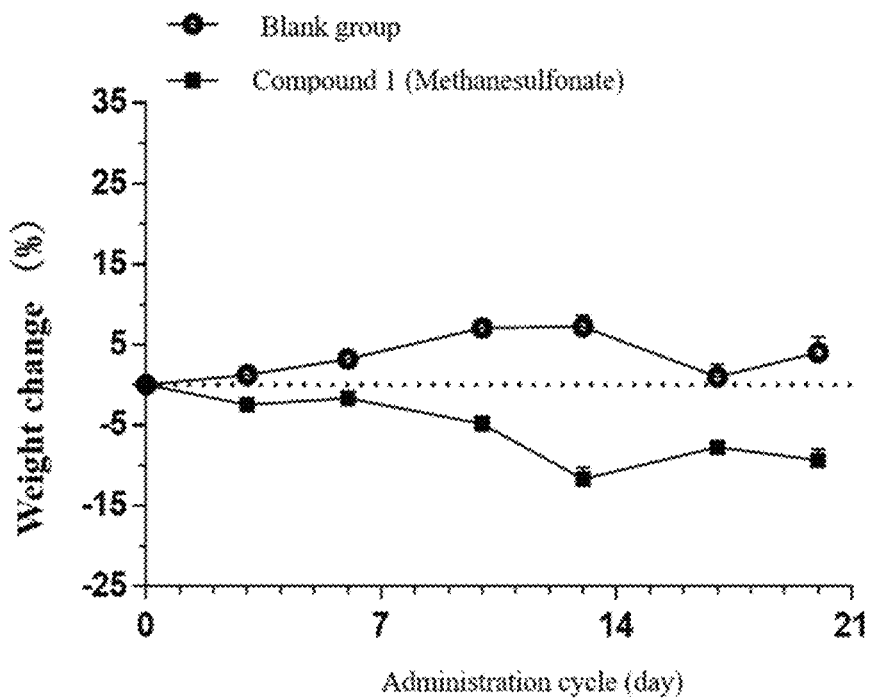
FIG. 2 shows the weight changes of tumor-bearing mice in human lung cancer NCI-H1975 mice subcutaneous xenograft tumor model during administration.

Experimental Results:

see FIGS. 1, 2 and Table 6.

Experimental Conclusions:

From FIGS. 1, 2 and the tumor volume data in Table 6, it can be seen that the compounds of the present disclosure have significant anti-tumor efficacy, and the TGI can reach 105%, achieving the effect of shrinking tumors.

Table 6 Inhibitory effect of compounds against human lung cancer cell H1975

TABLE 6

Inhibitory effect of compounds against human lung cancer cell H1975 subcutaneous xenograft tumor model

| Groups | Tumor volume $(mm^3)^a$ (Day 0) | Tumor volume $(mm^3)^a$ (Day 20) | RTV | TGI (%) | T/C (%) |
|---|---|---|---|---|---|
| Blank | 153 ± 6 | 2419 ± 196 | 16.01 ± 1.72 | — | — |
| Compound 1 | 153 ± 7 | 33 ± 16 | 0.20 ± 0.10 | 105.3 | 1.35 % |

Notes:
$^a$Mean ± standard error, n = 6.

Experimental Embodiment 6 Growth Inhibitory Effect of Compounds in Mouse Ba/F3 EGFR D770_N771 Ins SVD Subcutaneous Allograft Tumor Model Experimental Purposes:

Ba/F3 (EGFR-D770_N771insSVD) cells were artificially constructed cell lines with EGFR-D770_N771insSVD insertion mutation using mouse B cells. The CDX model established by this cell line was used to evaluate the inhibitory effect of preferred compounds on Exon 20 EGFR-D770_N771insSVD insertion mutation in animals.

Experimental Materials:

Nude mouse (BALB/c Nude), Ba/F3 (EGFR-D770_N771insSVD) cell line

Experimental Method:

1. Cell culture: cells were cultured in vitro in monolayer, culture conditions were RPMI-1640 (cell culture medium) with 10% fetal bovine serum, 100 U/mL penicillin and 100 g/mL streptomycin, the cells were cultured at a 37° C., 5% $CO_2$ incubator. Conventional digestion with trypsin-EDTA was performed twice a week for passage. When the saturation of Ba/F3 (EGFR-D770_N771insSVD) cell was 80%-90%, and the number reached the requirement, the cells were harvested and counted. The density was 5×106 cells.

2. Cell inoculation: 0.2 mL (containing 5×$10^6$ cells) of Ba/F3 (EGFR-D770_N771insSVD) cell suspension (PBS:Matrigel=1:1) was inoculated subcutaneously on the right back of each mouse, for a total of 64 mice. On the 7th day after inoculation, when the average tumor volume reached 133 $mm^3$, the randomized stratified grouping method was used to start the grouping administration according to the tumor volume and animal weight. PBS was phosphate buffer and Matrigel was matrix.

3. Administration: The dose was 0-7 days: 10 mg/kg, 8-21 days: 40 mg/kg; oral administration; administration frequency: once a day×3 weeks.

Tumor Measurements and Experimental Indexes

Tumor diameters were measured with vernier calipers twice a week. The calculation formula of tumor volume was: $V=0.5a \times b^2$, wherein a and b represented the long and short diameters of the tumor, respectively.

The antitumor efficacy of the compounds was evaluated by TGI (%) or relative tumor proliferation rate T/C (%).

Relative tumor proliferation rate T/C (%)=$T_{RTV}/C_{RTV}$×100% ($T_{RTV}$: mean RTV in the treatment group; $C_{RTV}$: mean RTV in the solvent control group).

The relative tumor volume (RTV) was calculated according to the results of tumor measurement. The calculation formula was RTV=$V_t/V_0$, wherein $V_0$ was the tumor volume measured at the time of group administration (i.e., $D_0$), and $V_t$ was the tumor volume corresponding to a certain measurement. $T_{RTV}$ and $C_{RTV}$ were taken on the same day.

TGI (%), reflecting the tumor growth inhibition rate. TGI (%)=[(1−(average tumor volume at the end of administration of a treatment group−average tumor volume at the beginning of administration of this treatment group))/(average tumor volume at the end of treatment in the solvent control group−average tumor volume at the beginning of treatment of the solvent control group)]×100%.

After the experiment, the tumor weight will be detected, and T/C (%) will be calculated. T and C represented the tumor weight of the administration group and the solvent control group, respectively.

Figure 3:
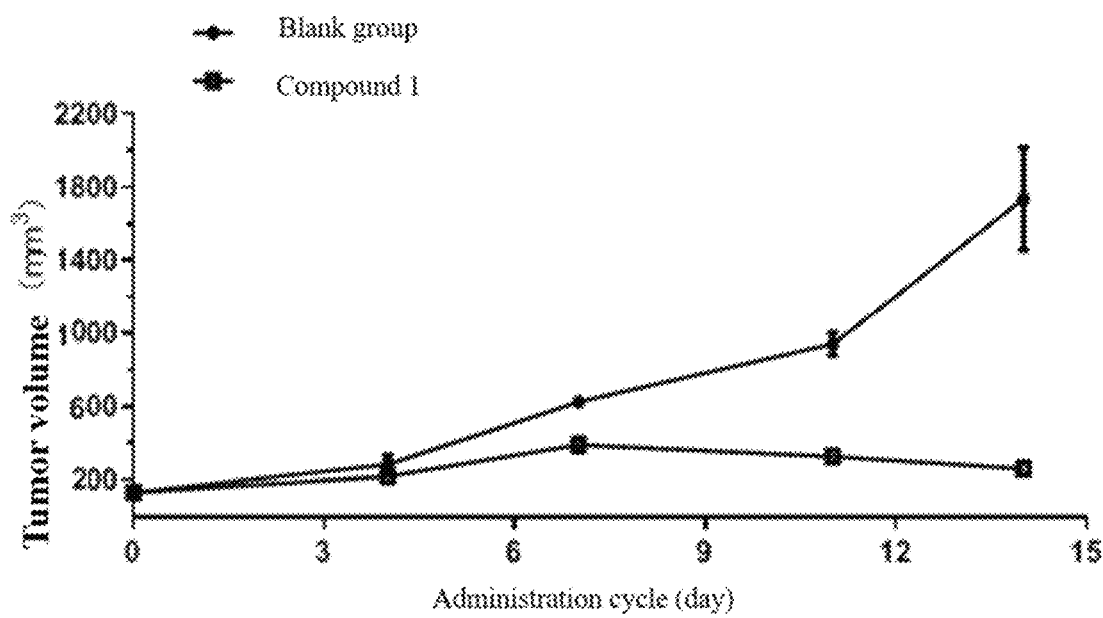
FIG. 3 shows the tumor growth curve of Ba/F3 EGFR D770_N771 ins SVD subcutaneous allograft tumor model.
Figure 4:
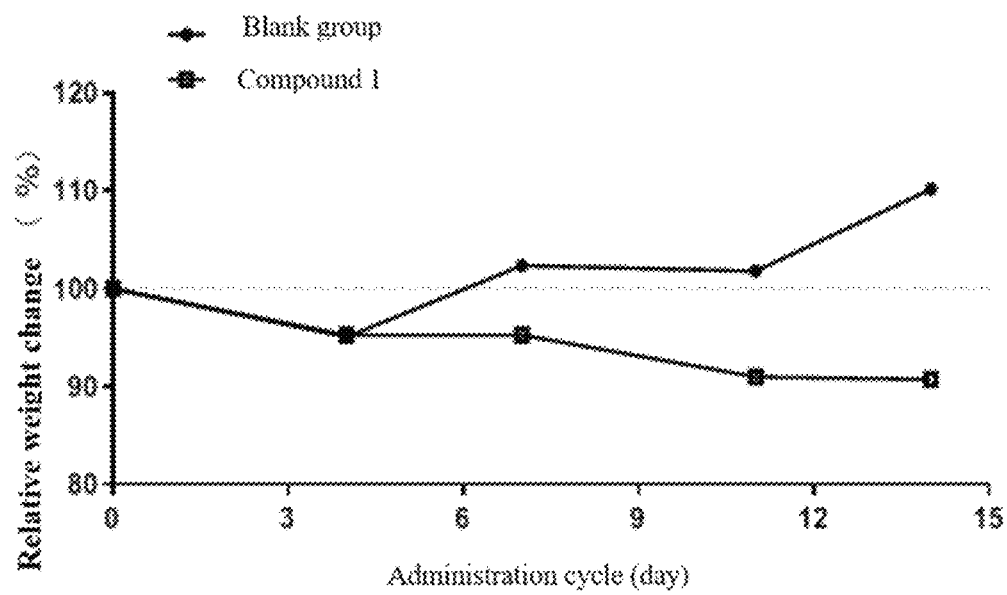
FIG. 4 shows the weight changes of tumor-bearing mice in Ba/F3 EGFR D770_N771 ins SVD subcutaneous allograft tumor model during administration.

Experimental Results:
see Table 7 and FIGS. 3 and 4.

TABLE 7

Inhibitory effect of compounds against Ba/F3 (EGFR-D770_N771insSVD) subcutaneous allograft tumor model

| Groups | Tumor volume (mm³)[a] (Day 0) | Tumor volume (mm³)[a] (Day 14) | RTV | TGI (%) | T/C (%) |
|---|---|---|---|---|---|
| Blank | 133.5 ± 7.6 | 1734.7 ± 281.7 | 13.0 | — | — |
| Compound 1 | 133.2 ± 8.2 | 259.1 ± 35.2 | 1.9 | 92.1 | 14.9 |

Notes:
[a]Mean ± standard error, n = 6.

Experimental Conclusions:

As seen in FIGS. 3 and 4 and the tumor volume data in Table 7, the compounds of the present disclosure have significant inhibition effect on tumor growth in an in vivo pharmacodynamic model of Ba/F3 (EGFR-D770_N771insSVD) subcutaneous allograft tumors.

Embodiment 7 Growth Inhibitory Effect of Compound Against HuPrime® Lung Cancer LU0387 Subcutaneous Xenograft BALB/C Female Nude Mouse Model Experimental Purposes:

The antitumor effects of the test drug in HuPrime® lung cancer LU0387 subcutaneous xenograft BALB/C nude mouse were evaluated.

Experimental Materials:

BALB/c Nude mice, female, 7-8 weeks, HuPrime® lung cancer xenograft model LU0387 tumor-bearing mouse tumor tissue.

Experimental Methods:

BALB/c nude mice were subcutaneously inoculated with HuPrime® model LU0387 tumor blocks to establish a human lung cancer subcutaneous transplantation tumor model. The test was divided into a solvent control group and a test drug group. The drug was administered by gavage, once daily for 21 days. Efficacy was evaluated based on relative tumor inhibition rate (TGI), and the safety was evaluated based on animal weight change and mortality.

Tumor Measurements and Experimental Indexes

Tumor diameters were measured with vernier calipers twice a week. The calculation formula of tumor volume was: V=0.5a×b², wherein a and b represented the long and short diameters of the tumor, respectively.

The antitumor efficacy of the compounds was evaluated by TGI (%) or relative tumor proliferation rate T/C (%).

Relative tumor proliferation rate T/C (%)=$T_{RTV}/C_{RTV}$×100% ($T_{RTV}$: mean RTV in the treatment group; $C_{RTV}$: mean RTV in the solvent control group).

The relative tumor volume (RTV) was calculated according to the results of tumor measurement. The calculation formula was RTV=$V_t/V_0$, wherein $V_0$ was the tumor volume measured at the time of group administration (i.e., $D_0$), and $V_t$ was the tumor volume corresponding to a certain measurement. $T_{RTV}$ and $C_{RTV}$ were taken on the same day.

TGI (%), reflecting the tumor growth inhibition rate. TGI (%)=[(1−(average tumor volume at the end of administration of a treatment group−average tumor volume at the beginning of administration of this treatment group))/(average tumor volume at the end of treatment in the solvent control group−average tumor volume at the beginning of treatment of the solvent control group)]×100%.

After the experiment, the tumor weight will be detected, and T/C (%) will be calculated. T and C represented the tumor weight of the administration group and the solvent control group, respectively.

Figure 5:
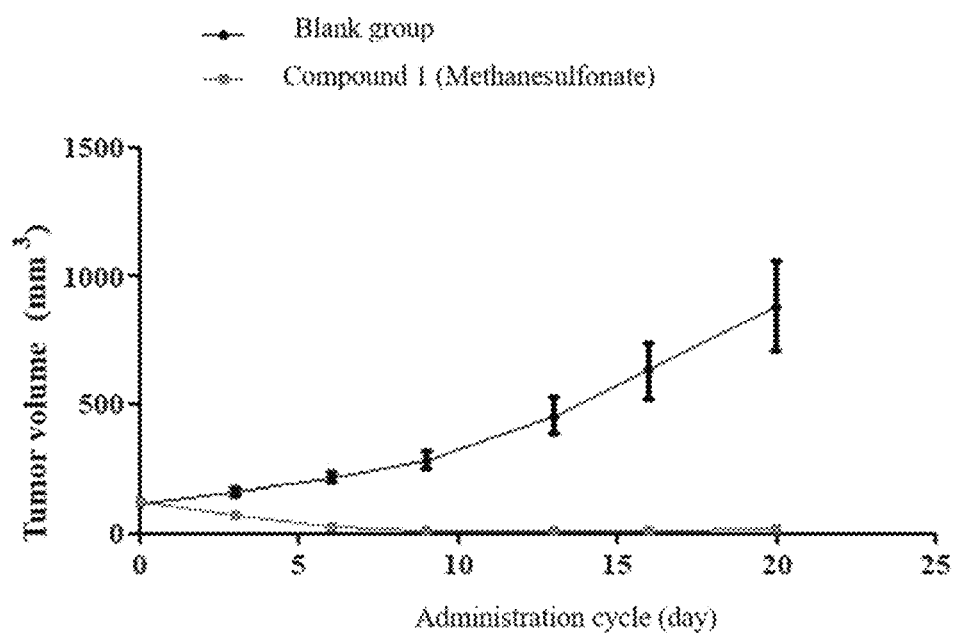
FIG. 5 shows the tumor growth curve of HuPrime lung cancer LU0387 mice subcutaneous xenograft tumor model.
Figure 6:
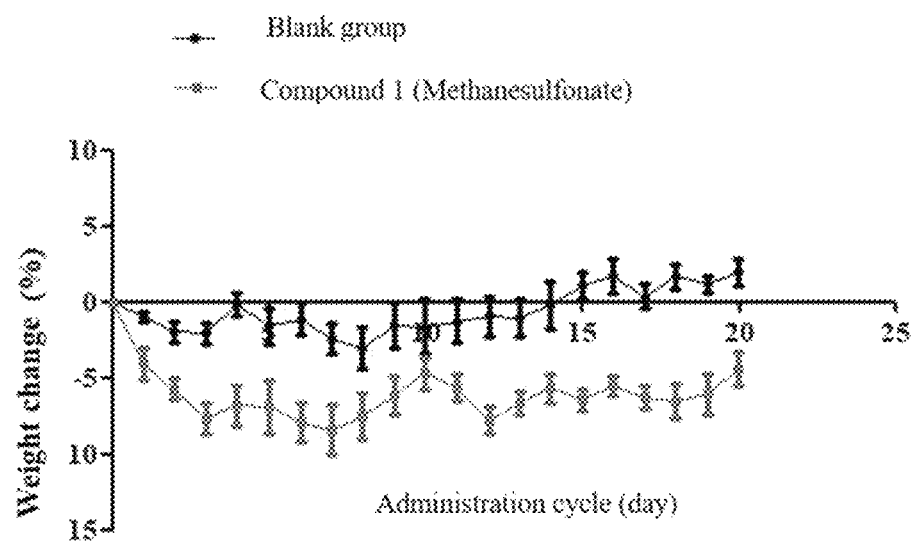
FIG. 6 shows the weight changes of tumor-bearing mice in HuPrime lung cancer LU0387 mice subcutaneous xenograft tumor model during administration.

Experimental Results:
see Table 8 and FIGS. 5 and 6.

Experimental Conclusions:

As seen in FIGS. 5 and 6 and the tumor volume data in Table 8, the compounds of the present disclosure have significant growth inhibition in tumor against HuPrime® lung cancer LU0387 subcutaneous xenograft BALB/c nude mice animal model with TGI=114%, achieving a tumor shrinking effect.

TABLE 8

Tumor inhibition effect against HuPrime® lung cancer LU0387 model

| Groups | Tumor volume (mm³)[a] (Day 0) | Tumor volume (mm³)[a] (Day 20) | RTV | TGI (%) | T/C (%) |
|---|---|---|---|---|---|
| Blank | 120.20 ± 4.06 | 883.6 ± 175.2 | 7.38 ± 1.51 | — | — |
| Compound 1 | 122.13 ± 3.12 | 16.97 ± 10.54 | 0.14 ± 0.08 | 114 | 2 |

Notes:
[a]Mean ± standard error, n = 6.

Experimental Embodiment 8 Pharmacokinetic Study of Single Intravenous and Oral Administration in Mice, Rats and Beagle Dogs Experimental Purposes:

The purpose of this experiment was to investigate the pharmacokinetics (PK) of the compounds in different species after single intravenous and single oral administration of the test compounds.

Sample Collection and Preparation:

After intravenous or oral administration, blood samples were collected from the animals, and the actual time of blood collection was recorded. After the blood samples were collected, the samples were immediately transferred to the labelled centrifuge tube containing K2-EDTA, and then centrifuged to obtain plasma. Plasma was transferred to pre-cooled centrifuge tubes, quick-frozen in dry ice and stored in an ultra-low temperature refrigerator at −70±10° C. until LC-MS/MS analysis was performed.

Pharmacokinetic Data Analysis:

The plasma drug concentration data of the compounds were processed using pharmacokinetic software with a non-compartmental model. The peak concentration ($C_{max}$) and time to peak ($T_{max}$), as well as the quantifiable end time were obtained directly from the plasma concentration-time curve. The following pharmacokinetic parameters were calculated using the log-linear trapezoidal method: half-life ($T_{1/2}$), apparent volume of distribution ($V_{dss}$), and clearance (Cl), area under the time-plasma concentration curve from point 0 to the end time point ($AUC_{0-last}$), and initial concentration ($C_0$).

Experimental Results:

see Table 9-1, Table 9-2, Table 9-3

TABLE 9-1

Pharmacokinetic parameters of single intravenous and oral administration of different doses in mice

| Administration method | PK parameters in mice | Compound 1 |
|---|---|---|
| Intravenous injection | Dose (mg/kg/day) | 2 |
| | Cl (mL/kg/min) | 57.7 |
| | $V_{dss}$ (L/kg) | 6.95 |
| | Exposure of AUC (nmol * h/L) | 884 |
| | $T_{1/2}$ (h) | 1.76 |
| Oral | Dose (mg/kg/day) | 10 |
| | $C_{max}$ (nmol) | 300 |
| | $T_{max}$ (h) | 2.00 |
| | Exposure of $AUC_{0-last}$ (nmol * h /L): | 1421 |
| | Oral bioavailability (%) | 22.1 |

TABLE 9-2

Pharmacokinetic parameters of single intravenous and oral administration of different doses in rats

| Administration method | PK parameters in rats | Compound 1 | | | |
|---|---|---|---|---|---|
| Intravenous injection | Dose (mg/kg/day) | 2 | | | |
| | Cl (mL/kg/min) | 90.5 | | | |
| | $V_{dss}$ (L/kg) | 18.0 | | | |
| | Exposure of AUC (nmol * h/L) | 548 | | | |
| | $T_{1/2}$ (h) | 2.62 | | | |
| Oral | Dose (mg/kg/day) | 10 | 20 | 50 | 200 |
| | Exposure of $AUC_{0-last}$ (nmol * h/L) | 593 | 3132 | 9394 | 18913 |
| | Oral bioavailability (%) | 21.6 | 57.1 | 68.6 | 34.5 |

TABLE 9-3

Pharmacokinetic parameters of single intravenous and oral administration of different doses in Beagle dogs

| Administration method | PK parameters in Beagle dogs | Compound 1 | |
|---|---|---|---|
| Intravenous injection | Dose (mg/kg/day) | 2 | |
| | Cl (mL/kg/min) | 12.7 | |
| | $V_{dss}$ (L/kg) | 7.98 | |
| | Exposure of AUC (nmol * h/L) | 3854 | |
| | $T_{1/2}$ (h) | 8.79 | |
| Oral | Dose (mg/kg/day) | 10 | 50 |
| | Exposure of $AUC_{0-last}$ (nmol * h/L) | 10307 | 35292 |
| | Oral Bioavailability (%) | 53.5 | 36.6 |

Experimental Conclusion:

The compounds of the present disclosure has good oral absorption, high exposure, good bioavailability and good PK property in mice, rats and dogs.

The invention claimed is:

1. A compound represented by formula (I) or a pharmaceutically acceptable salt thereof,

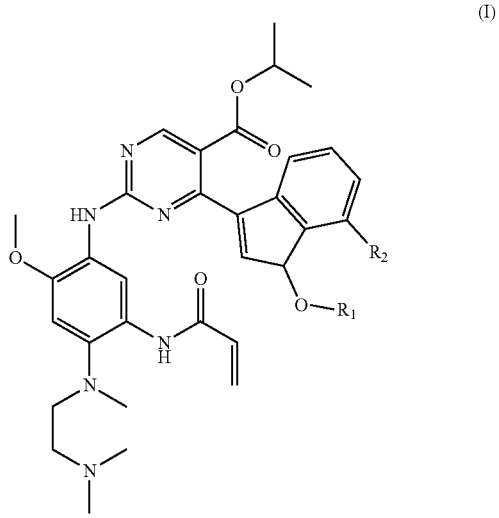

(I)

wherein, $R_1$ is selected from $C_{1-3}$ alkyl, $R_2$ is selected from H, F, Cl, Br, I, $C_{1-3}$ alkyl and cyclopropyl.

2. The compound or the pharmaceutically acceptable salt thereof according to claim 1, wherein, $R_1$ is selected from methyl, ethyl and isopropyl.

3. The compound or the pharmaceutically acceptable salt thereof according to claim 1, wherein, $R_2$ is selected from H, Cl and cyclopropyl.

4. A compound represented by the following formula or a pharmaceutically acceptable salt thereof,

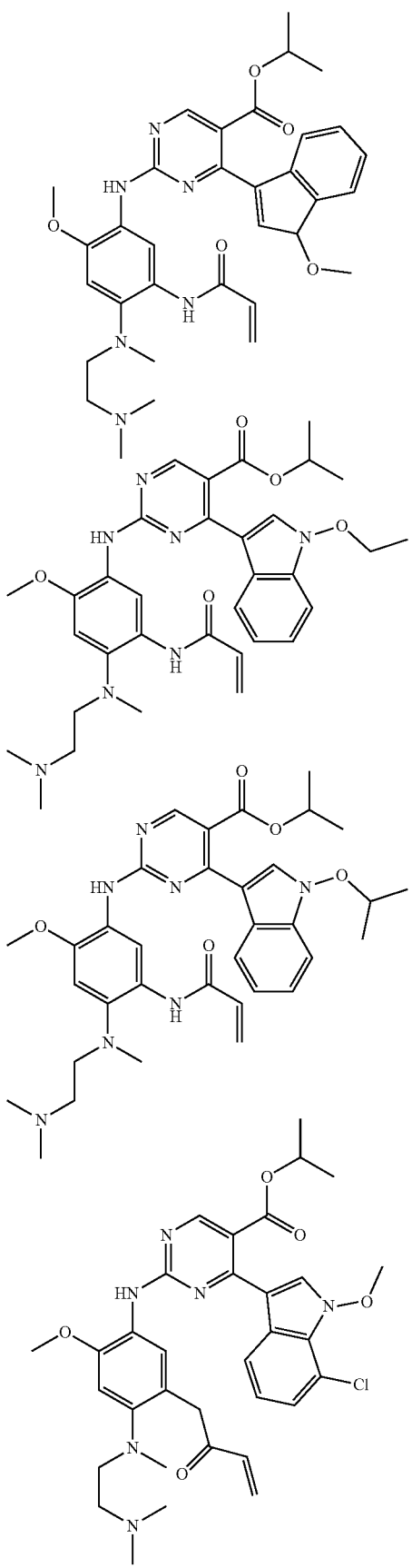
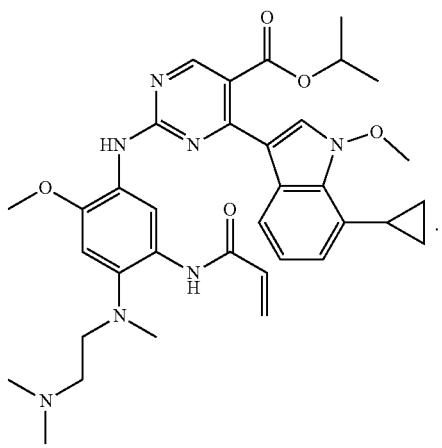
5. The compound or the pharmaceutically acceptable salt thereof according to claim 4, wherein, the pharmaceutically acceptable salt thereof is selected from
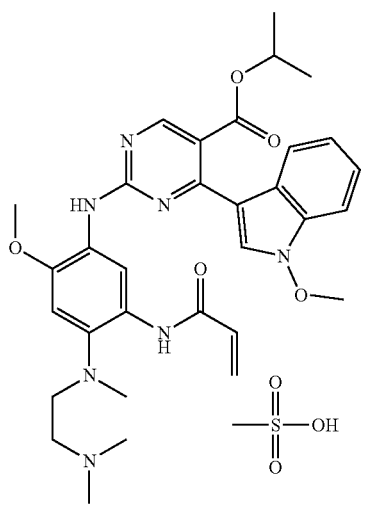
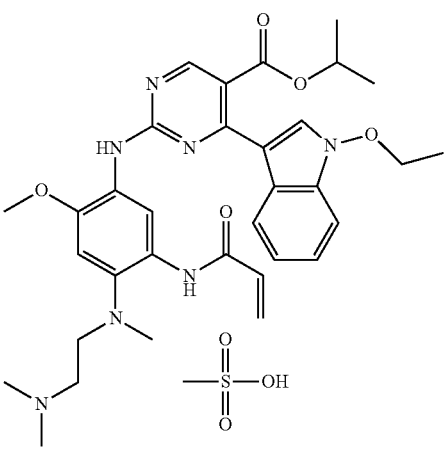

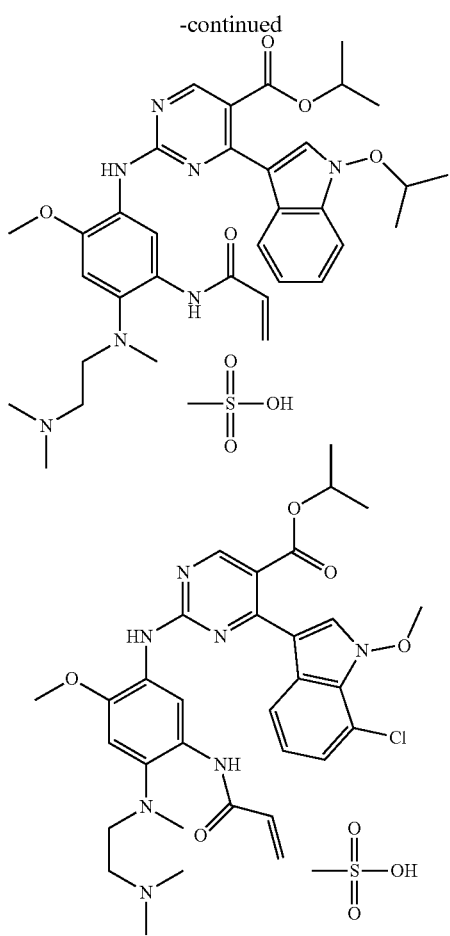

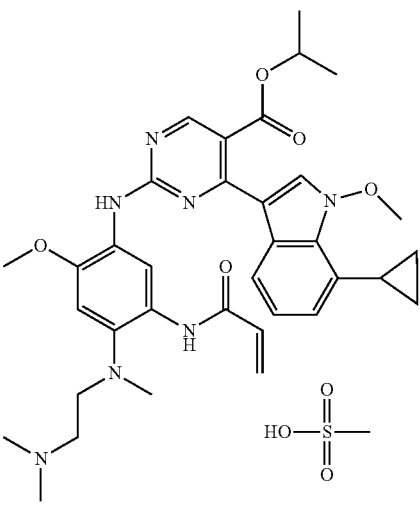

6. A pharmaceutical composition comprising a therapeutically effective amount of the compound or the pharmaceutically acceptable salt thereof according to claim 1 as the active ingredient and a pharmaceutically acceptable carrier.

7. The compound or the pharmaceutically acceptable salt thereof according to claim 2, wherein, $R_2$ is selected from H, Cl and cyclopropyl.

* * * * *